US007850305B2

(12) United States Patent
Hirohara et al.

(10) Patent No.: US 7,850,305 B2
(45) Date of Patent: Dec. 14, 2010

(54) APPARATUS AND METHOD FOR MEASURING SPECTRUM IMAGE DATA OF EYEGROUND

(75) Inventors: Yoko Hirohara, Tokyo (JP); Tatsuo Yamaguchi, Tokyo (JP); Toshifumi Mihashi, Tokyo (JP); Hiroyuki Aoki, Tokyo (JP); Yasuko Tsuruga, Tokyo (JP)

(73) Assignee: Topcon Corporation, Tokyo (JP)

( * ) Notice: Subject to any disclaimer, the term of this patent is extended or adjusted under 35 U.S.C. 154(b) by 1411 days.

(21) Appl. No.: 11/292,277

(22) Filed: Dec. 2, 2005

(65) Prior Publication Data

US 2007/0002276 A1 Jan. 4, 2007

(30) Foreign Application Priority Data

Dec. 3, 2004 (JP) ............................. 2004-352092
Dec. 3, 2004 (JP) ............................. 2004-352093

(51) Int. Cl.
*A61B 3/14* (2006.01)
*A61B 3/10* (2006.01)

(52) U.S. Cl. ........................ 351/206; 351/210; 351/221

(58) Field of Classification Search ................ 351/200, 351/205–206, 210, 213, 221, 246
See application file for complete search history.

(56) References Cited

U.S. PATENT DOCUMENTS

2005/0157259 A1* 7/2005 Akita et al. ................. 351/206

(Continued)

FOREIGN PATENT DOCUMENTS

JP 2002-507445 A 3/2002

(Continued)

OTHER PUBLICATIONS

T. Mihashi et al., U.S. PTO Office Action, U.S. Appl. No. 11/812,079, Nov. 26, 2008, 23 pgs.

(Continued)

*Primary Examiner*—Scott J Sugarman
*Assistant Examiner*—Dawayne A Pinkney
(74) *Attorney, Agent, or Firm*—Foley & Lardner LLP

(57) ABSTRACT

The object of the invention is to provide a favorable spectral characteristic that reduces variation depending on the frequency of received light intensity, and that is gentle on a subject eye. It also eliminates displacement between positions of respective spectral images of the same part even if a change in alignment occurs between the eye and apparatus with the lapse of time. An apparatus 1 for measuring spectral fundus image data of this invention comprises: an illumination optical system 10 having an illumination light source 11 that emits a light beam in a specified wavelength range; a light receiving optical system 20 for forming a fundus image on the light receiving surface of a photographing section 4; a liquid crystal wavelength tunable filter 32 capable of choosing a wavelength of a transmitted light beam in a specified wavelength range; a spectral characteristic correction filter 13 having wavelength characteristic for correcting the wavelength characteristic of the emitted light intensity of the illumination light source 11 and the transmission wavelength characteristic of the wavelength tunable filter 32 so that the received light intensity on the light receiving surface is kept within the specified range; and a data measuring section 7 for taking the spectral fundus image data from the light receiving surface while changing the wavelength of the light beam passing through the wavelength tunable filter 32.

18 Claims, 22 Drawing Sheets

U.S. PATENT DOCUMENTS

2006/0276698 A1    12/2006    Halldorsson et al.

FOREIGN PATENT DOCUMENTS

WO    WO 99/48418 A1    9/1999

OTHER PUBLICATIONS

T. Mihashi et al., U.S. PTO Office Action, U.S. Appl. No. 11/812,081, Nov. 25, 2008, 17 pgs.

T. Mihashi et al., U.S. PTO Notice of Allowance, U.S. Appl. No. 11/812,079, dated Apr. 3, 2009, 8 pgs.

U.S. Appl. No. 11/812,079, filed Jun. 14, 2007, Mihashi et al.

U.S. Appl. No. 11/812,081, filed Jun. 14, 2007, Mihashi et al.

T. Mihashi et al., U.S. PTO Office Action, U.S. Appl. No. 11/812,079, May 12, 2008, 22 pgs.

T. Mihashi et al., U.S. PTO Office Action, U.S. Appl. No. 11/812,081, May 12, 2008, 20 pgs.

B. Khoobehi et al., "Hyperspectral Imaging for Measurement of Oxygen Saturation in the Optic Nerve Head", Investigative Ophthalmology and Visual Science, vol. 45, No. 5, May 2004, pp. 1464-1472.

* cited by examiner (a)

(b)

LEAST SQUARE MATCHING

APPARATUS AND METHOD FOR MEASURING SPECTRUM IMAGE DATA OF EYEGROUND

BACKGROUND OF THE INVENTION

1. Technical Field

This invention relates to an apparatus and method for measuring spectral fundus image data. In particular, it relates to an apparatus and method for measuring spectral fundus image data that make spectral characteristics uniform within a specified wavelength range. It also relates to an apparatus and method for measuring spectral fundus images data that coordinate a large number of image data taken at different time points with high accuracy over a specified wavelength range.

2. Related Art

Fundus observation is doubtless important in ophthalmic diagnosis. At present, anomaly findings are obtained by diagnosing the eye fundus by means of colored fundus images, fluorescent contrast images, etc. from a fundus camera. If it is possible to measure quantitatively oxygen saturation degree on the fundus and constituent substances distributed in the retina, there is a possibility of finding out the functions of fine parts of the retina, which is considered to be greatly useful in clinical applications. Further, if spectral distribution of substances in the retina is clarified by spectral analyses, there is a possibility of analyzing the substances in the retina from the spectral images.

However, most of the studies carried out up to now are far from in full-scale. Full-scale image measurement is considered to meet such conditions as: (a) being capable of obtaining high quality images, and (b) being capable of measuring spectral images with a higher degree of wavelength analysis over a wide wavelength band. Such an image measurement method is occasionally called hyper-spectral imaging. Advent of the liquid crystal wavelength tunable filter has made it possible to obtain spectral images relatively easily. Using a number of spectral images of different wavelengths makes it possible to examine spectral characteristics of substances in detail and to extract constituents having various known spectral distributions.

While full-scale measurement of the living organism is the subject for the future, preliminary studies have been carried out at two to four wavelengths or so on animals as models, in which measurements are used to confirm if this technique can cope with measuring the human eye. Besides, an examination is being carried out using an apparatus, that can be applied to the human eye, for obtaining spectral images of the fundus by separating light using a diffraction grating and scanning the fundus.

While the hyper-spectral imaging is a technique in the spotlight and is used to obtain spectral images of the fundus, it is hard to perform accurate analyses because the amount of light of spectral images obtained varies greatly by the wavelength. Moreover, the hyper-spectral light separation with a light amount without putting burden on humans has yet to be realized, and an apparatus enabling it has yet to be realized either.

As typical light separation devices, such ones may be enumerated as: the diffraction gratings, prisms, etalons, and filters. Up to now, diffraction gratings and prisms have been often used in spectral measurement of tunable wavelength. Recently, however, the advent of the liquid crystal wavelength tunable filter has made it possible to take spectral images at any wavelength and measure spectral images easily. Since the liquid crystal wavelength tunable filter is fundamentally a parallel flat plate, it can be easily installed in the optical system, and its optical performance can be easily maintained. Therefore, it is often used in obtaining spectral images using a microscope. It is also used in studies in which spectral images obtained are synthesized to create natural images.

However, there has been a problem of insufficient amount of light on the short wavelength side and excessive amount of light on the long wavelength side (in the range from 500 nm to 700 nm) due to spectral characteristics of the liquid crystal wavelength tunable filter, the light source (halogen lamp, etc.), and the CCD.

Besides, as restricted by for example the wavelength tunable time of the liquid crystal wavelength tunable filter and the exposure time of the camera, it takes about 20 seconds to take images at every 10 nm in the wavelength range from 510 nm to 720 nm. Because alignment between the eye and the apparatus varies during that time, there has been another problem that the spectral images taken of the same part are displaced from each other.

An object of this invention is to provide a spectral fundus images data measuring apparatus that reduces variation by the frequency in received light intensity, that keeps the received light intensity at the light receiving surface within a specified range, that is gentle on the subject eye, and that makes it possible to obtain favorable spectral characteristic.

Another object of this invention is to provide an apparatus and method for measuring spectral fundus images data that can eliminate position displacement between spectral images of the same part even if change in alignment occurs between the eye and the apparatus with the lapse of time.

Still another object of this invention is to provide an apparatus and method for measuring spectral fundus images data that can correct image positions almost fully automatically by a program using image correlation, and that can automate comparison between spectral images and display of spectral characteristics of characteristic points on the retina.

SUMMARY OF THE INVENTION

To solve the above problems, the spectral fundus images data measuring apparatus 1 of this invention, as shown in FIG. 1 for example, comprises an illumination optical system 10 having an illumination light source 11 that emits a light beam in a specified wavelength range, for illuminating a fundus of a subject eye with the light beam from the illumination light source 11; a light receiving optical system 20 for receiving the light beam reflected from the illuminated fundus F and for forming a fundus image on the light receiving surface of a photographing section 4; a wavelength tunable filter 32 disposed in 15 either the illumination optical system 10 or the light receiving optical system and capable of choosing a wavelength of a transmitted light beam in the specified wavelength range; a spectral characteristic correcting filter 13 disposed in either the illumination optical system 10 or the light receiving optical system 20 and having a wavelength characteristic for correcting the wavelength characteristic of the emitted light intensity of the illumination light source 11 and the transmission wavelength characteristic of the wavelength tunable filter 32 to keep the received light intensity on the light receiving surface within a specified range; and a data measuring section 7 for taking spectral fundus image data based on signals from the light receiving surface when the wavelength of the transmitted light beam of the wavelength tunable filter 32 is changed.

Here, while a CCD is preferable for the light receiving surface, it may be a CMOS. With the above constitution using the wavelength tunable filter, it is possible to obtain spectral images at any wavelength, and for the fundus image too, spectral image measurement becomes possible. Besides, employing the spectral characteristic correcting filter makes the apparatus gentle on the subject eye, and makes it possible to correct frequency-dependent variation in the received light intensity, keep the received light intensity on the light receiving surface within a specified range, and obtain favorable spectral characteristic.

In the apparatus 1 for measuring spectral fundus image data, as shown in FIG. 1 for example, the wavelength tunable filter 32 may be disposed in the light receiving optical system 20 and the spectral characteristic correcting filter 13 may be disposed in the illumination optical system 10.

The above constitution with the spectral characteristic correcting filter disposed in the illumination optical system makes it possible to illuminate the subject eye with light that is relatively uniform and of a small amount and measure in a manner gentle on the subject eye. Besides, disposing the wavelength tunable filter in the light receiving optical system makes it possible to reduce changes in color and amount of the light entering the eye.

In the apparatus 1 for measuring spectral fundus image data, as shown in FIG. 5 or FIG. 8 for example, the wavelength tunable filter 32 may be a liquid crystal wavelength tunable filter and the spectral characteristic correcting filter 13 may be constituted that its transmission rate in a specified wavelength range is higher on the shorter wavelength side than on the longer wavelength side.

With the above constitution, it is possible to choose any wavelength easily in the visible light range using the liquid crystal wavelength tunable filter. It is also possible to realize spectral characteristic excellent in uniformity by correcting the spectral characteristics of the liquid crystal wavelength tunable filter and the halogen lamp using the spectral characteristic correcting filter.

In the apparatus 1 for measuring spectral fundus image data, the specified wavelength range is preferably 540 to 610 nm.

The above constitution can provide data useful for the spectral analysis of substances in the retina.

In the apparatus 1 for measuring spectral fundus image data, the light receiving surface is preferably made of a CCD and the specified range of the received light intensity is preferably within a dynamic range of the CCD.

The above constitution using the spectral characteristic correcting filter together with the CCD camera facilitates photographing with the CCD camera and enables automation of exposure.

The apparatus for measuring spectral fundus image data may further comprise, as shown in FIG. 2 for example, an exposure control section 81 constituted to determine automatically the exposure time according to the received light signal level on the light receiving surface.

The above constitution makes it possible to change the exposure time of the camera according to the light amount every time of photographing and obtain images further excellent in spectral characteristic by correcting the spectral characteristic of the optical system. Using it together with the spectral characteristic correcting filter makes it possible to obtain images of further improved spectral characteristic.

To solve the above problems, an apparatus 1 for measuring spectral fundus image data, comprises, as shown in FIG. 1 for example: an illumination optical system 10 for illuminating a fundus F of a subject eye E; a light receiving optical system 20 for receiving a light beam reflected from the illuminated fundus F and for forming a fundus image on a light receiving surface of a photographing section 4; and a data measuring section 7 for comparing with each other a plurality of fundus image original data taken at different time points based on signals from the light receiving surface to correct positions of the images, and for producing a series of fundus image data with their positions corrected.

Here, while the CCD is preferable for the light receiving surface, it may be a CMOS. The above constitution can eliminate position displacement of the same part between respective spectral images by correcting the variation in alignment between the eye and the apparatus with the lapse of time.

In the apparatus 1 for measuring spectral fundus image data, the correction of positions of the images may be, as shown in FIG. 14 for example, performed as position matching between a plurality of the spectral fundus image original data using correlation processing and affine transformation or Hermert transformation while choosing characteristic points.

Here, the characteristic point is in some cases linear. Constituting in this way makes it possible to correct with high accuracy the change in the alignment between the eye and the apparatus with the lapse of time. Besides, the correction may be made almost fully automatically with a program using the image correlation.

In the apparatus 1 for measuring spectral fundus image data, as shown in FIG. 1 for example, the illumination optical system 10 may include an illumination light source 11 that emits a light beam in a specified wavelength range; and the apparatus 1 may further comprise a wavelength tunable filter 32 disposed in either the illumination optical system 10 or the light receiving optical system 20 and capable of choosing a wavelength of a transmitted light beam in the specified wavelength range; and in the apparatus 1, the data measuring section 7 may take a plurality of the fundus image original data by changing a wavelength of the light beam transmitted through the wavelength tunable filter 32.

With the above constitution, the position displacement between respective spectral images for the same part may be eliminated by correcting the change in alignment between the eye and the apparatus with the lapse of time. Moreover, using the wavelength tunable filter makes it possible to obtain spectral images at any wavelengths and measure spectral images for fundus images. Employing the spectral characteristic correcting filter makes the apparatus gentle on the subject eye, and makes it possible to obtain favorable spectral characteristic by correcting frequency-dependent variation of received light intensity.

The apparatus 1 for measuring spectral fundus image data, as shown in FIG. 1 for example, may further comprises a spectral characteristic correcting filter 13 disposed in either the illumination optical system 10 or the light receiving optical system 20 and having a wavelength characteristic for correcting the wavelength characteristic of emitted light intensity of the illumination light source 11 and the transmission wavelength characteristic of the wavelength tunable filter 32 to keep the received light intensity on the light receiving surface within a specified range.

The above constitution with the spectral characteristic correcting filter disposed in the illumination optical system makes it possible to illuminate the subject eye with relatively uniform and less amount of light and perform measurement that is gentle on the subject eye. Besides, disposing the wavelength tunable filter in the light receiving optical system can reduce changes in color and amount of the light entering the eye.

In the apparatus 1 for measuring spectral fundus image data as recited in claim 9, the amount of change in the wavelength chosen at the wavelength tunable filter 32 may be set to be equal to or smaller than a threshold value; and the data measuring section 7 may correct the positions of the images while comparing with each other the fundus images original data different in wavelength by the amount of change equal to or smaller than the threshold value.

With the above constitution, when the amount of change in wavelength is small, less change occurs in the light intensity of the spectral fundus image original data, and two fundus image original data for the same part are easy to correlate therebetween to facilitate correction of position. Therefore, restricting the wavelength change amount as described above makes the position correction easy with high accuracy. Applying it to many images in succession makes it possible to obtain a series of fundus images data in which image positions are in agreement with high accuracy.

In the apparatus 1 for measuring spectral fundus image data, the specified wavelength range is preferably 540 to 610 nm, and the amount of change equal to or smaller than the threshold value is preferably 10 nm.

The above constitution provides data useful for the spectral analysis of substances in the retina.

In the apparatus 1 for measuring spectral fundus image data, the wavelength tunable filter 32 is preferably a liquid crystal wavelength tunable filter.

The above constitution using the liquid crystal wavelength tunable filter makes it possible to choose any wavelength easily in the visible light range.

In the apparatus 1 for measuring spectral fundus image data, the data measuring section 7 preferably chooses, as the characteristic point, a blood vessel part on the shorter wavelength side and the choroid blood vessel part on the longer wavelength side to correct positions of the images.

The above constitution makes it possible to determine easily the characteristic point as a reference for position correction, and to correct positions with high accuracy.

In the apparatus 1 for measuring spectral fundus image data, the data measuring section 7 is preferably capable of calculating the received light intensity and optical density (also referred to as OD in this specification) of artery and vein.

With the above constitution, it is possible to provide, through the OD data, data that are useful for the spectral analysis of substances in the retina.

In the apparatus 1 for measuring spectral fundus image data, the data measuring section 7 preferably makes corrections according to a diameter of a blood vessel of a part where intensities at the artery and vein are calculated, calculates ODs in respective positions on the retina, analyzes factors of ODs in respective positions based on spectral distribution of ODs of the artery and vein, calculates rates of oxygenated hemoglobin in respective positions, and makes the oxygenated hemoglobin rates into a map.

The above constitution enables automatic analysis of the saturation degree of oxygen.

To solve the above problems, a method for measuring spectral fundus image data, as shown in FIG. 13 for example, comprises the steps of: illuminating a fundus F of a subject eye E of an animal with a light beam from an illumination light source 11 emitting the light beam in a specified wavelength range (S001); receiving a reflected light beam from the fundus F and forming an animal fundus image on a light receiving surface of a photographing section 4 (S002); placing a liquid crystal wavelength tunable filter 32 capable of choosing a wavelength of a transmitted light beam in a specified wavelength range in either an illumination optical system 10 or a light receiving optical system 20 to change a wavelength of the light beam transmitted through the liquid crystal wavelength tunable filter 32 and taking spectral fundus image data based on the signals from the light receiving surface (S003); and comparing with each other spectral fundus image original data different in wavelength by an amount of change smaller than a threshold value, and producing a series of spectral fundus image data in the specified wavelength range in a data measuring section 7 (S604).

The above constitution can corrects the change in alignment between the eye and the apparatus with the lapse of time and eliminate the position displacement between respective spectral images for the same part. Moreover, using the liquid crystal wavelength tunable filter enables acquisition of spectral images at any wavelength and also enables spectral image measurement for fundus images. Besides, employing the spectral characteristic correcting filter makes it possible to make the measurement gentle on the subject eye, and obtain favorable spectral characteristic with the variation by the frequency in the received light intensity corrected.

In the method for measuring spectral fundus image data, preferably, when positions of the images are corrected; an original data the second shortest in wavelength with respect to a reference image the shortest in wavelength, out of the spectral fundus image original data, is used as a pre-correction image, the position of which is corrected; next, using the position-corrected pre-correction image as a new reference image, another original data the third shortest in wavelength is used as another pre-correction image, the position of which is corrected; followed by successive correction of positions from shorter wavelength side to longer wavelength side, or, an original data the second longest in wavelength with respect to a reference image the longest in wavelength, out of the spectral fundus images original data, is used as a pre-correction image, the position of which is corrected; next, using the position-corrected pre-correction image as a new reference image, another original data the third longest in wavelength is used as another pre-correction image, the position of which is corrected; followed by successive correction of positions from longer wavelength side to shorter wavelength side.

Here, in the following case, the above method is to be applied with the wavelength range divided into two. In one wavelength range, an image near the median of the measurement wavelength range is assumed to be a reference image, a next original data of a longer wavelength is assumed to be a pre-correction image, and its position is corrected. The corrected image is assumed to be a new reference image and a next original data of a longer wavelength is assumed to be a pre-correction image, and its position is corrected. In this way, positions are corrected in succession from short to long wavelengths up to the longest wavelength. After that, in the wavelength range, the image near the median of the measurement wavelength range is assumed again to be the reference image, a next original data of a shorter wavelength is assumed to be a pre-correction image, and its position is corrected. The corrected image is assumed to be a new reference image and a next original data of a shorter wavelength is assumed to be a pre-correction image, and its position is corrected. In this way, positions are corrected in succession from long to short wavelengths down to the shortest wavelength. The above is similar to the case in which the positions are corrected in succession, first from the wavelength near the median to shorter wavelengths and then from the wavelength near the median to longer wavelengths.

With the above constitution, when the amount of change in wavelength is small, less change occurs in the light intensity of the spectral fundus image original data, and two fundus image original data for the same part are easy to so that positions are corrected easily. Therefore, it is possible to obtain a series of fundus images data with their positions in agreement with high accuracy by successively correcting positions with reduced amount of change in wavelength.

In the method for measuring spectral fundus image data, preferably, as shown in FIG. 19, the spectral fundus image original data images are taken in the specified wavelength range of 540 to 610 nm and with the amount of change in wavelength chosen at the liquid crystal wavelength tunable filter 32 being set to 10 nm (S502); the step of correcting the image positions having the steps of, choosing characteristic points of spectral fundus image original data different in wavelength from each other by an amount corresponding to a change less than a threshold value to match their positions by carrying out correlation processing and affine transformation or Hermert transformation (S503), choosing artery and vein as characteristic points to calculate received light intensities and ODs of the artery and vein (S505), calculating ODs in respective positions on the retina (S507) by corrections according to the blood vessel diameters in parts where the intensities at the artery and vein are calculated (S506), calculating the rates of oxygenated hemoglobin in respective positions on the retina by analyzing factors of ODs in respective positions on the retina on the basis of spectral distribution of ODs of the artery and vein (S508), and making the rates of oxygenated hemoglobin of the spectral fundus images into a map (S509).

The above constitution provides useful data for the spectral analysis of the substances in the retina and enables automatic analysis of the oxygen saturation degree.

This invention makes it possible to provide an apparatus and method of measuring spectral fundus images data that correct frequency-dependent variation in the received light intensity, keep the received light intensity on the light receiving surface within a specified range, and are gentle on the subject eye and capable of obtaining favorable spectral characteristic.

This invention provides an apparatus and method of measuring spectral fundus images data that can eliminate position displacement between respective spectral images for the same part by correcting the change in alignment between the eye and the apparatus with the lapse of time.

This invention further provides an apparatus and method of measuring spectral fundus images data capable of almost full automatically correcting image positions by a program using image correlation and of automating the comparison between spectral images and displaying spectral characteristics of characteristic points on the retina.

This application is based on the Patent Applications No. 2004-352092 filed on Dec. 3, 2004 and 2004-352093 filed on Dec. 3, 2004 in Japan, the contents of which are hereby incorporated in its entirety by reference into the present application, as part thereof.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

The use of the terms "a" and "an" and "the" and similar referents in the context of describing the invention (especially in the context of the following claims) are to be construed to cover both the singular and the plural, unless otherwise indicated herein or clearly contradicted by context. The use of any and all examples, or exemplary language (e.g., "such as") provided herein, is intended merely to better illuminate the invention and does not pose a limitation on the scope of the invention unless otherwise claimed.

DETAILED DESCRIPTION OF THE PREFERRED EMBODIMENT

Embodiments of the present invention are described below in reference to the drawings.

Figure 1:
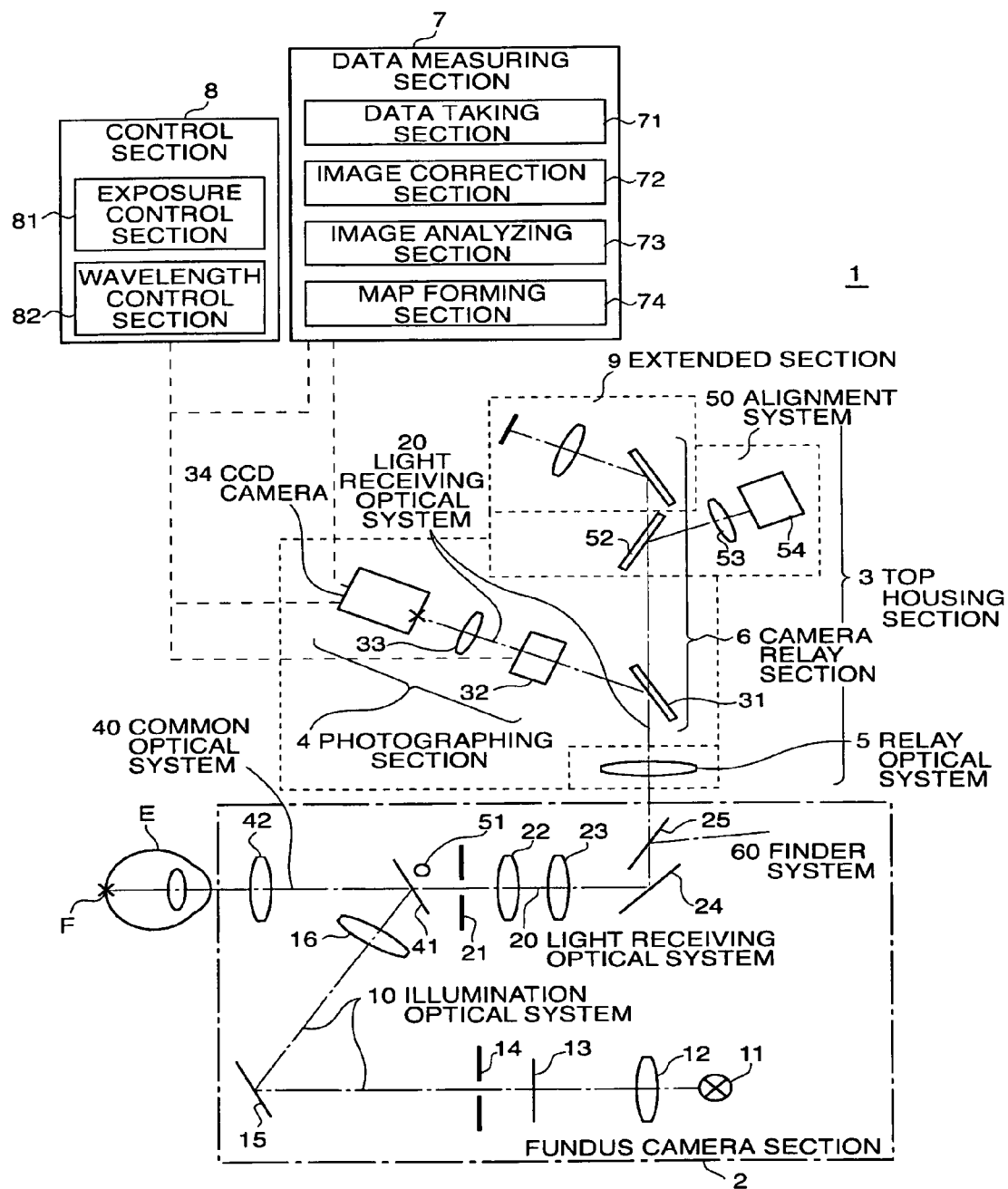
FIG. 1 shows an example constitution of a spectral fundus images data measuring apparatus as an embodiment of the invention.

FIG. 1 shows a general example of an optical system of a spectral fundus image data measuring apparatus 1 as an embodiment of the invention. In FIG. 1, the spectral fundus images data measuring apparatus 1 may be roughly divided into: a fundus camera section 2, a top housing section 3, a data measuring section 7, and a control section 8. The fundus camera section 2 is made up of: an illumination optical system 10 for illuminating the fundus F of a subject eye E, the fore stage section of a light receiving optical system 20 for receiving light beam reflected from the fundus F and forming a fundus image on the light receiving surface of a photographing section 4, a finder optical system 60 for an optometrist to observe the fundus F, etc. The top housing 3 is made up of: the photographing section 4 for photographing a spectral fundus image, an alignment optical system 50 for aligning the illumination position of the illumination light on the fundus F (a light source 51 is provided at the fundus camera section 2), a relay optical system 5 for collimating the reflected light beam received from the fundus camera section 2 and leading it to a camera relay section 6, and the camera relay section 6 for transmitting the reflected light beam having passed through the relay optical system 5 to various light receiving means such as the photographing section 4. The hinder stage section of the light receiving optical system 20 is made up of the relay optical system 5, the camera relay section 6, and the photographing section 4. An extended section 9 above the camera relay section 6 is a section for extended use by connecting various light receiving means such as a monitor TV, a hard copier, etc. to the light receiving optical system 20.

In the fundus camera section 2, the illumination optical system 10 is made up by disposing successively on its illumination optical axis: a halogen lamp 11 as an illumination light source, a condenser lens 12, a spectral characteristic correcting filter 13, a diaphragm 14, a mirror 15, a relay lens 16, and a beam splitter 41. Here, the halogen lamp 11 is placed near the front focal point of the condenser lens 12 and emits a wide wavelength range of light beam. The diaphragm 14 is disposed in a position to be conjugate with respect to the beam splitter 41.

The illumination optical system 10 further leads the light beam reflected from the beam splitter 41 through an objective lens 42 to illuminate the fundus F of the subject eye E. The area from the beam splitter 41 to the subject eye E constitutes an optical system 40 common to the illumination optical system 10 and light receiving optical system 20.

The light receiving optical system 20 is made up by disposing successively on the reflected light optical axis passing through the subject eye E: the objective lens 42, the beam splitter 41, an iris diaphragm 21, a focusing lens 22, an image forming lens 23, a mirror 24, a switching mirror 25; and is connected to the light receiving optical system of the top housing section 3. The iris diaphragm 21 is disposed in a position to be conjugate with the fore-end part of the subject eye E. When spectral images are to be taken, the switching mirror 25 is removed from the optical path, with for example a solenoid.

The alignment optical system 50 is to align the illumination light with the illuminated position on the fundus F, and is made up of: a dichroic mirror 52, an image forming lens 53, and a monitoring camera 54, to observe reflected light when light is cast from the alignment light source 51 (provided in the fundus camera section 2) to the eye. The wavelength of the alignment light source 51 is set to be near infrared (for example 940 nm) so that alignment may be carried out without affecting the spectral images in the visible light range even when spectral images are being taken. The dichroic mirror 52 allows visible light (for example 750 nm or shorter in wavelength) to pass through and reflects light of longer wavelengths. When the dichroic mirror 52 is used as a switching mirror and removed with for example a solenoid when spectral images are not being taken, it is possible with the extended section 9 to observe the fundus in color. The monitoring camera 54 may be for example a CCD camera. The finder optical system 60 is for an optometrist to observe the fundus F with the unaided eye.

In the top housing section 3, the light receiving optical system 20 has the relay optical system 5 placed on the axis of light reflected from the subject eye E, so that the light beam reflected from the fundus F is led through the relay optical system 5 into the camera relay section 6. In the camera relay section 6, a dichroic mirror 31 is placed on the reflected light axis to reflect visible light (for example 750 nm or shorter in wavelength) and allows light on the longer wavelength side to pass through. The light beam reflected from the dichroic mirror 31 is led to the photographing section 4. In the photographing section 4 are placed on the axis of light reflected from the dichroic mirror 31: a liquid crystal wavelength tunable filter 32, an image forming lens 33, and a CCD camera 34 having a light receiving surface. The light receiving surface is disposed to be conjugate with respect to the fundus F of the subject eye E, so that the fundus images are focused on the light receiving surface. The image forming lens 33 is to relay the light coming out of the liquid crystal wavelength tunable filter 32 to the CCD camera. Using the liquid crystal wavelength tunable filter 32 makes it possible to easily choose any wavelength in the visible light range and so facilitate analysis of the spectral characteristics.

The data measuring section 7 is made up of: a data taking section 71 for taking spectral fundus images data according to signals from the light receiving surface of the CCD camera 34, an image correcting section 72 for matching image positions, an image analyzing section 73 for analyzing spectral retinal images, and a map forming section 74 for plotting oxygenated hemoglobin rates or the like into a map; and stores programs for image matching flow and spectral retinal image analysis flow. The image analyzing section 73 makes corrections according to the blood vessel diameters of parts where intensities at the artery and vein are calculated, calculates optical densities (hereinafter called ODs) in positions on the retina, analyzes factors of ODs in respective positions on the retina based on the spectral distribution of ODs of artery and vein, and calculates rates of oxygenated hemoglobin in respective positions on the retina.

The control section 8 controls, in order to measure spectral fundus images data, the entire spectral fundus images data measuring apparatus 1, including: actions of the fundus camera section 2, the top housing section 3, and the data measuring section 7; and the flow of data and signals. It also has an exposure control section 81 for controlling the exposure of the CCD camera and a wavelength control section 82 for controlling the wavelength of the liquid crystal wavelength tunable filter, and stores programs for the flow of taking spectral fundus images and the flow of setting exposure time for the CCD camera. Incidentally, the control section 8 may be embodied with an ordinary personal computer.

Next is described the spectral characteristic of the optical system of the spectral fundus images data measuring apparatus of the embodiment. For the analysis of the spectral characteristics, mainly a wavelength range of 430 to 950 nm is used, within which the spectral characteristic, as uniform as possible, is preferable. Factors that affect greatly the spectral characteristic are thought to be the CCD camera 34, the liquid crystal wavelength tunable filter 32, and the halogen lamp 11. Spectral characteristics of the respective devices are described below.

In this embodiment, a dispersion-type light separating method is employed. While the Fourier-type light separation method can be named as one other than the dispersion-type light separation method, the dispersion-type light separation method is employed because of concern about noise on the images of a retina with the Fourier-type light separation method that uses interference. Incidentally, the Fourier light separation method may also be used because it can separate light instantaneously and is advantageous in terms of the amount of light.

The reasons for using a halogen lamp as the illumination light source 11 are that it emits light over a wide range of wavelength from visible light to near infrared rays, that continuous lighting for about 10 seconds is required to separate light in time sequence, and that improvement on CCDs has made it possible to take images without using a flash.

Figure 2:
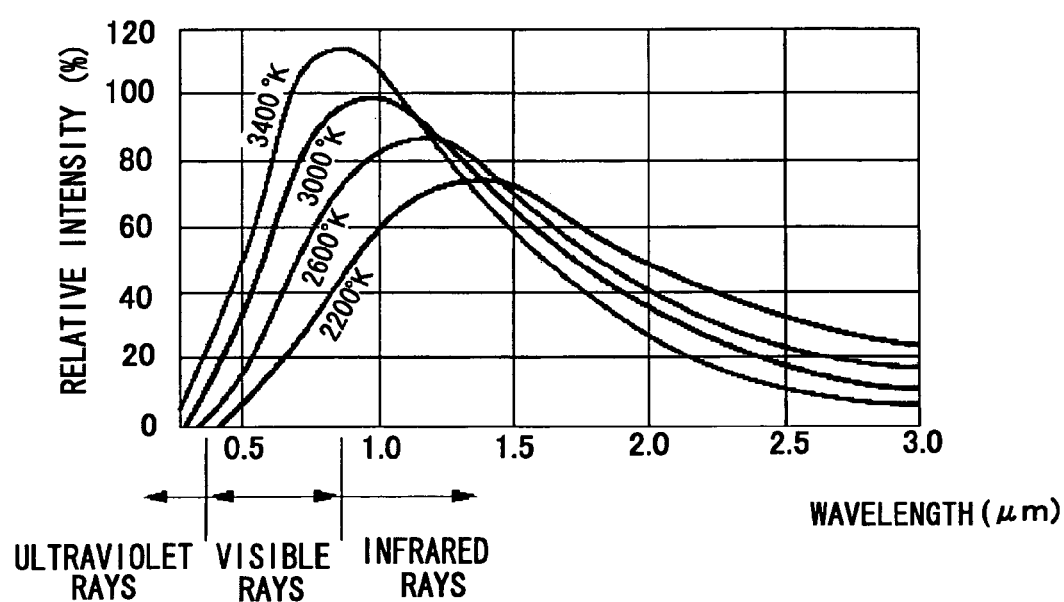
FIG. 2 shows an example of spectral characteristic of a halogen lamp.

FIG. 2 shows an example of spectral characteristic of a halogen lamp as the illumination light source 11. The horizontal axis represents wavelength (μm) and the vertical axis relative intensity (%). Spectral characteristics over the color temperature range from 2200 to 3400° K are shown assuming that the maximum of the curve for 3000° K to be 100%. As seen from FIG. 2, the illumination light of the halogen lamp is useful for spectral analysis because the light continuously covers a wavelength range from visible to infrared rays. The intensity of the illumination light source 11 in the visible light range increases monotonically with the increase in wavelength.

Figure 3:
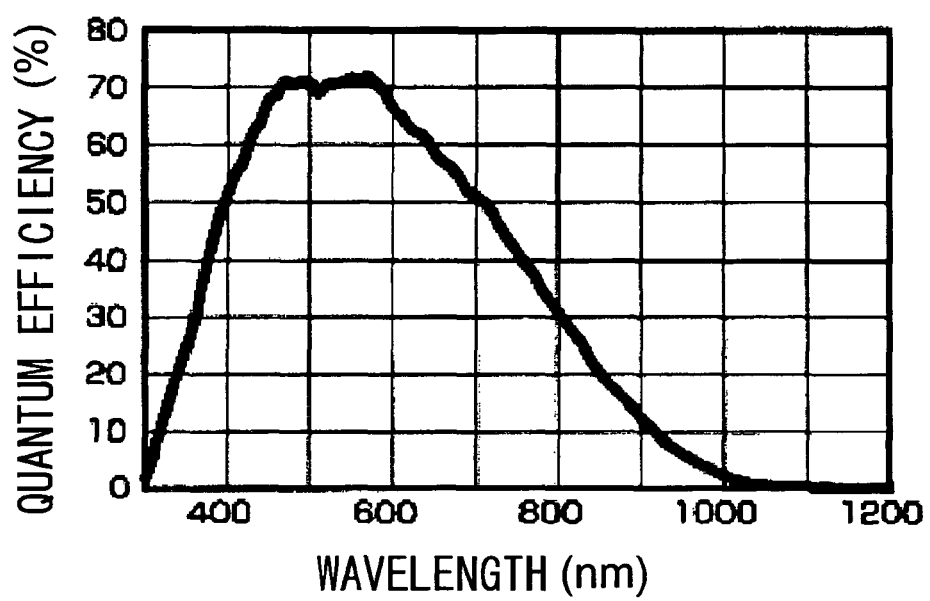
FIG. 3 shows an example of spectral sensitivity characteristic of a CCD camera.

FIG. 3 shows the spectral sensitivity characteristic of the CCD camera 34. The horizontal axis represents wavelength (nm) and the vertical axis quantum efficiency (%). The CCD camera 34 has sensitivity over a wide range of wavelength from visible light to near infrared range, is capable of obtaining high-definition images for example of 1,300,000 pixels (1344×1024) and of reading at a high speed (about 8 frames/sec) with low noise. There is an approximately flattened peak of sensitivity, in the wavelength range between 450 to 600 nm, decreasing on both sides of the peak.

Figure 4:
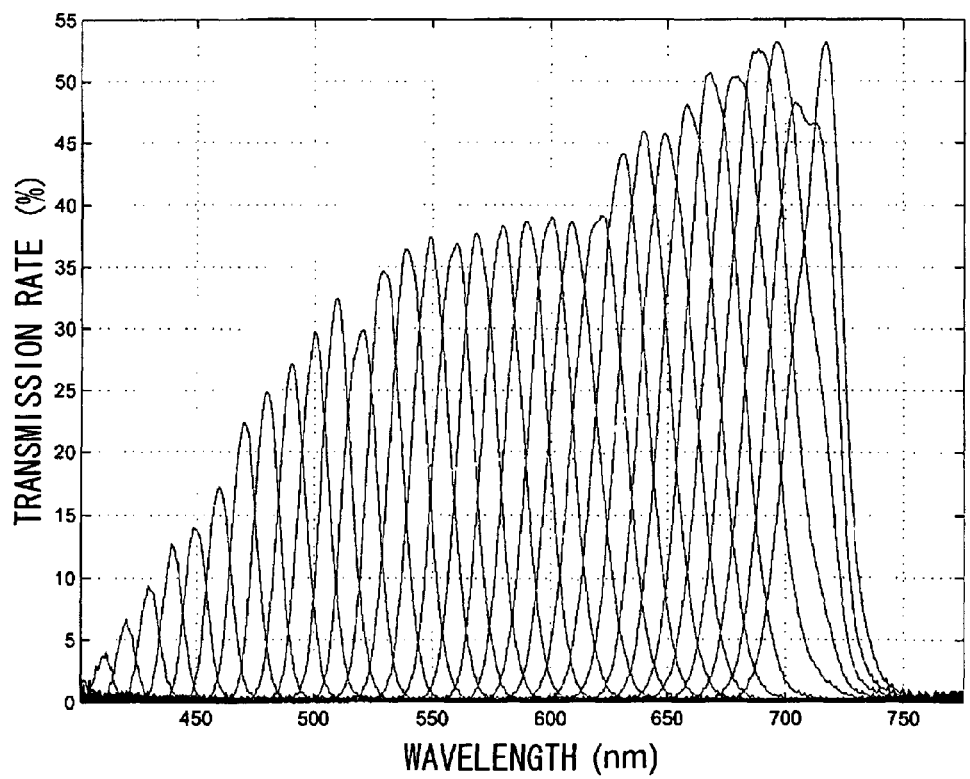
FIG. 4 shows an example of band-pass characteristic of a liquid crystal wavelength tunable filter.

FIG. 4 shows an example of band-pass characteristic of the liquid crystal wavelength tunable filter 32. The horizontal axis represents wavelength (nm) and the vertical axis transmission rate (%). As for the liquid crystal wavelength tunable filter 32, its transmission wavelength may be chosen in the range from 400 to 720 nm by changing the voltage applied to the liquid crystal. FIG. 4 shows how the transmission light changes when the transmission center wavelength is changed at 10 nm intervals. The width of the transmission light is about 20 nm. The peak value of the transmission light increases approximately monotonically with the increase in the wavelength.

Figure 5:
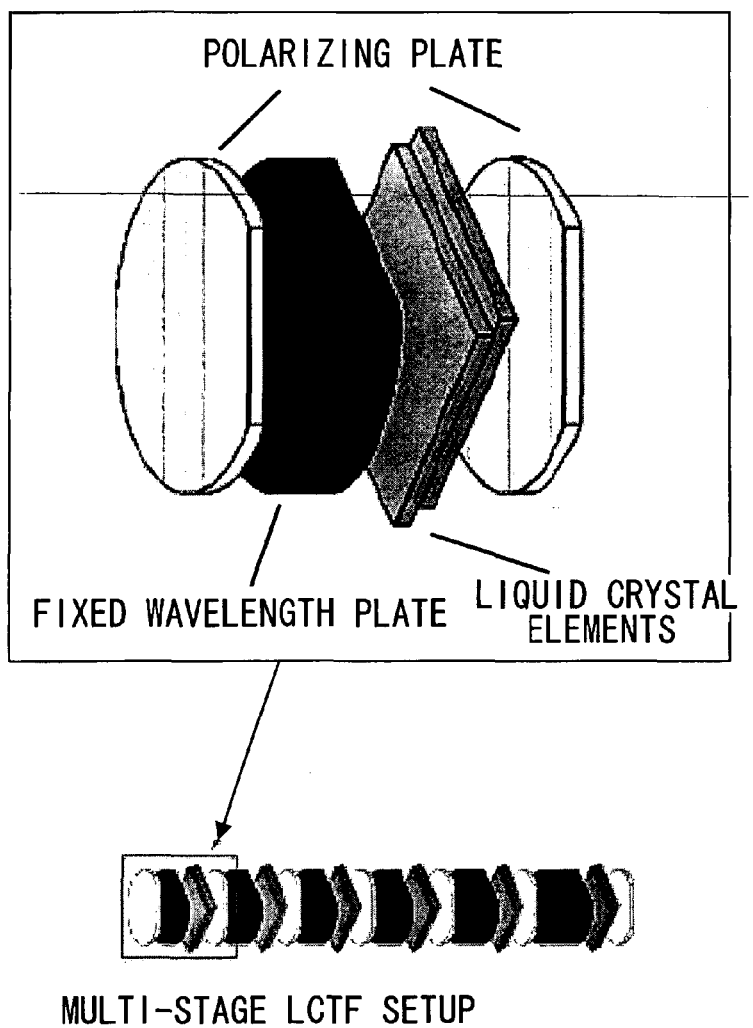
FIG. 5 shows an example constitution of the liquid crystal wavelength tunable filter.

FIG. 5 shows an example constitution of the liquid crystal wavelength tunable filter 32. In the liquid crystal wavelength tunable filter, the wavelength can be chosen by combining together several stages of liquid crystal tunable filters (LCTFs). As shown in FIG. 5, one LCTF is made up by placing a constant wavelength plate and a liquid crystal tunable wavelength plate between two polarizing plates. The angles formed by the constant wavelength plate and the liquid crystal tunable wavelength plate to the polarizing plate is fixed to 45° so that the optical path difference between ordinary ray and extraordinary ray produced may be controlled by the liquid crystal tunable wavelength plate.

When one wavelength plate is assumed to have a thickness d, the optical path difference R between the ordinary ray and extraordinary ray is expressed with the equation (1):

$$R = d \times (n(e) - n(o)) \qquad \text{Equation (1)}$$

where n(o) is the refraction index for the ordinary ray, and n(e) for the extraordinary ray. When the constant wavelength plate and the liquid crystal wavelength tunable plate are combined and the voltage applied to the liquid crystal wavelength tunable plate is changed, the optical path difference R changes. Light of an optical path difference R is taken out in 45° direction through the polarizing plate to form an interference filter.

An overall transmission rate T is expressed as the equation (2) assuming the wavelength to be λ, and the rate changes depending on the optical path difference R:

$$T = \frac{1}{2} \cos^2\left(\frac{\pi R}{\lambda}\right) \qquad \text{Equation (2)}$$

Figure 6:
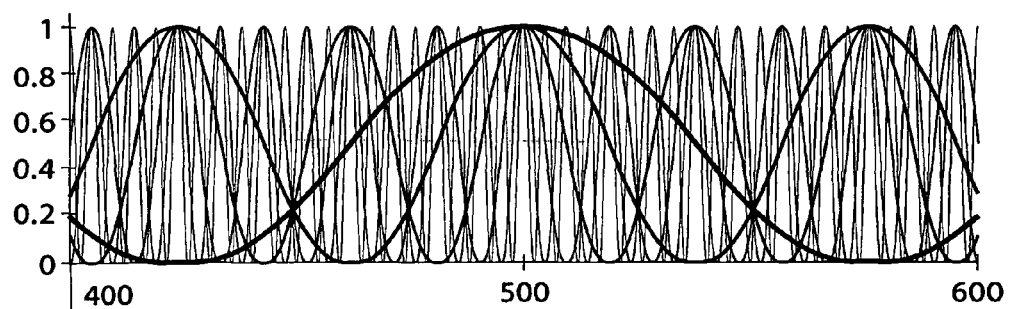
FIG. 6 shows an example of a method for choosing the wavelength of the liquid crystal wavelength tunable filter.
Figure 6:
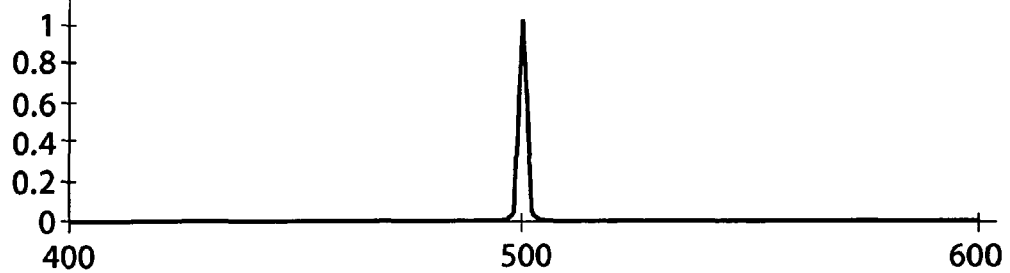

FIG. 6 shows an example of wavelength choosing method with the liquid crystal wavelength tunable filter 32. Wavelength plates of different thicknesses are combined to narrow the output wavelength width, and the combinations are stacked in several stages (six stages for the example shown) to realize a wavelength width of 20 nm. FIG. 6(a) shows the filter characteristic of each of the LCTFs superposed in six stages. FIG. 6(b) shows the filter characteristic of the liquid crystal wavelength tunable filter 32 made by superposing six stages of the LCTFs. The transmission center wavelength may be arbitrarily changed quickly by changing the voltage applied to the liquid crystal tunable wavelength plate of each LCTF, so that light of any intended wavelength component may be extracted.

Since the liquid crystal wavelength tunable filter 32 is affected with the direction of polarization of the incident light, alignment appropriate for the polarization angle of the incident light is required when polarized light is used. In that case too, the light emerging out of the liquid crystal wavelength tunable filter 32 is maintained in the same direction of polarization as the incident light.

Figure 7:
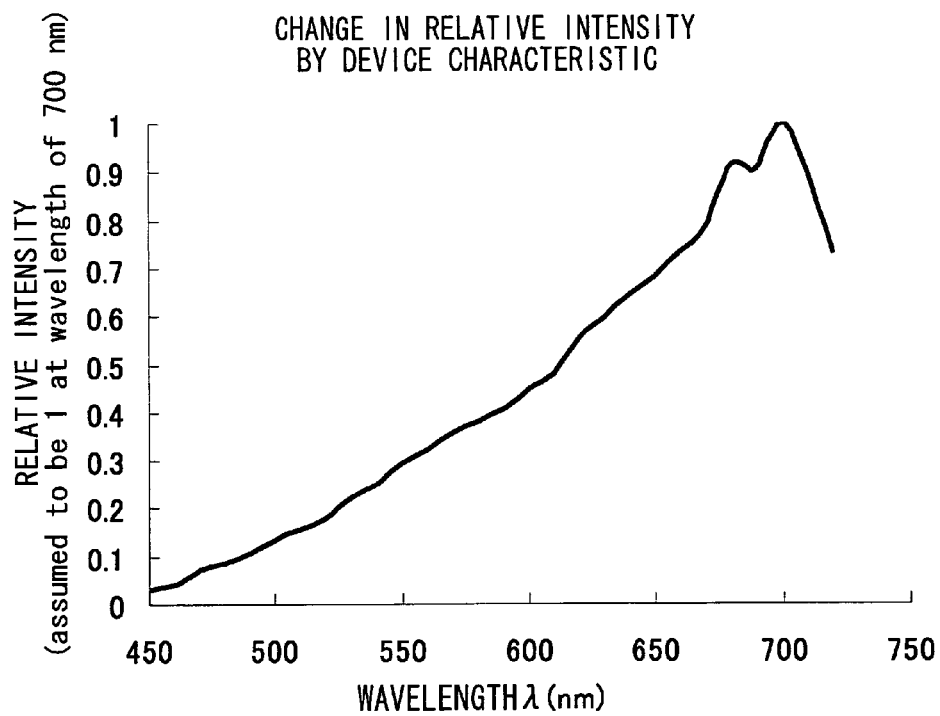
FIG. 7 shows an example of spectral characteristic with characteristics of the halogen lamp, liquid crystal wavelength tunable filter, and CCD camera added.

FIG. 7 shows an example of spectral characteristic to which spectral characteristics of the halogen lamp 11, the liquid crystal wavelength tunable filter 32, and the CCD camera 34 are added. The horizontal axis represents wavelength (nm) and the vertical axis relative intensity (assuming the light intensity at the wavelength 700 nm to be one). It is seen that the relative intensity almost monotonically increases in the range between 450 and 700 nm. As shown, the characteristic of all the optical components combined together is low on the shorter wavelength side and steeply increases toward the longer wavelength side. In order to counter this tendency, the spectral characteristic correcting filter 13 is required.

Figure 8:
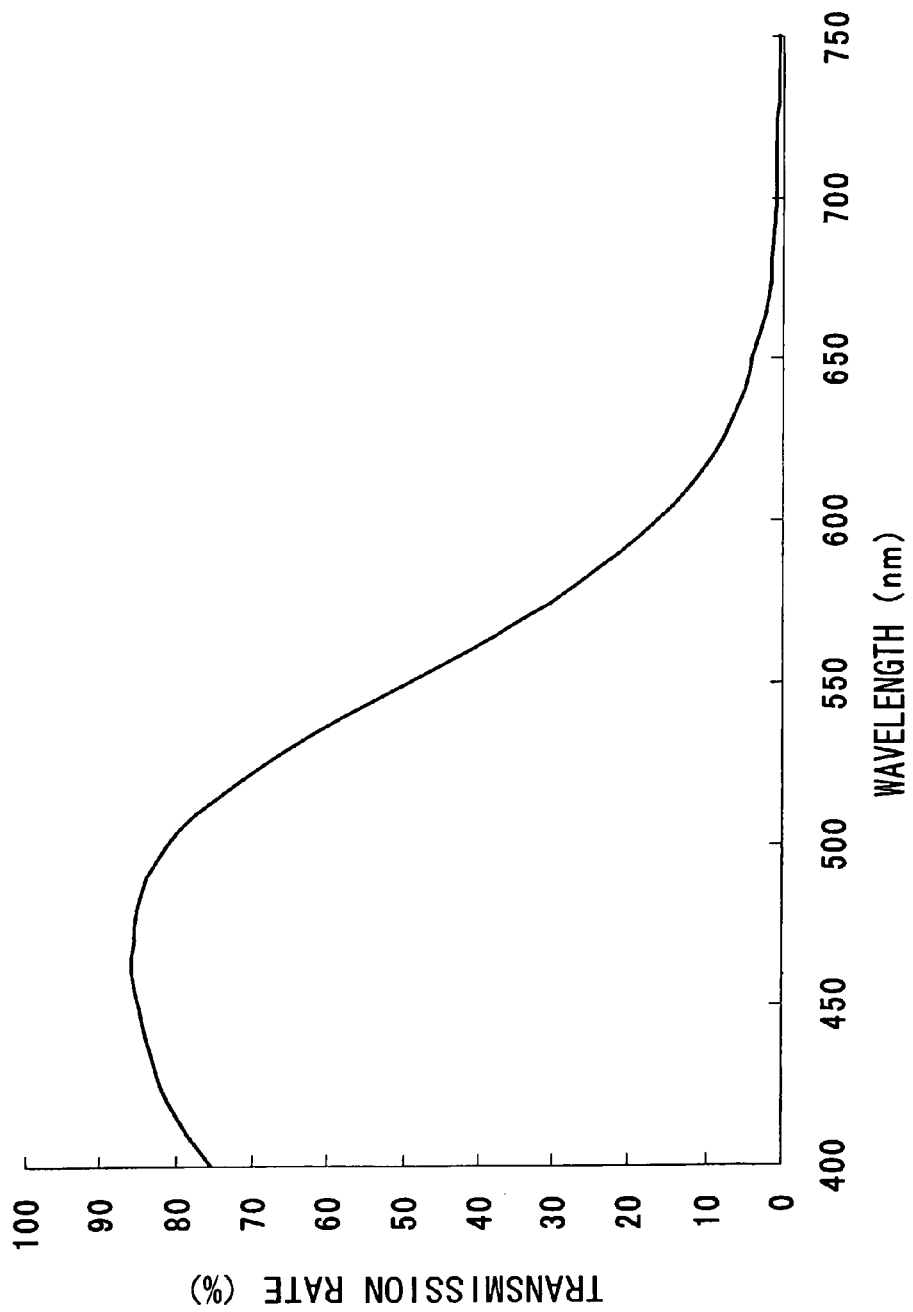
FIG. 8 shows an example of spectral characteristic of a spectral characteristic correcting filter.

FIG. 8 shows an example of the spectral characteristic of the spectral characteristic correcting filter 13. The horizontal axis represents wavelength (nm) and the vertical axis transmission rate (%). In this embodiment, a filter of a transmission center wavelength of 460 nm is chosen to make correction in the range between 450 and 700 nm.

Figure 9:
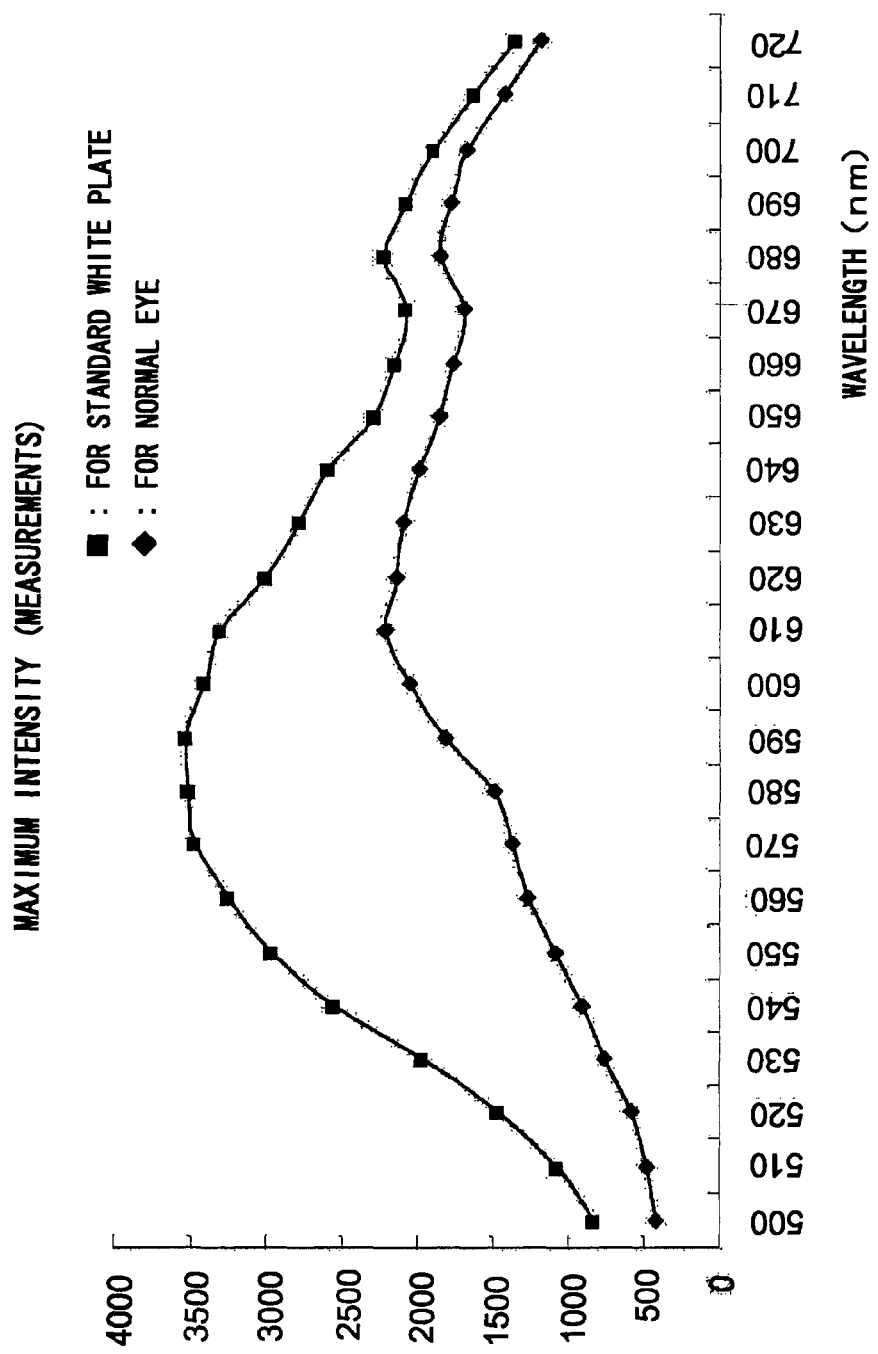
FIG. 9 shows an example of spectral characteristic of an optical system with the spectral characteristic correcting filter inserted.

FIG. 9 shows an example of spectral characteristic of an optical system in which the spectral characteristic correcting filter 13 is inserted. The horizontal axis represents wavelength (nm) and the vertical axis maximum intensity obtained with the CCD camera 34. In this example, a maximum value is made at 12 bit, 4096. The data are the measurements of the maximum intensity of spectral images for a normal eye and a standard white plate with a constant exposure time (for example 200 ms) after inserting the spectral characteristic correcting filter 13. The diamond dots ♦ represent the maximum intensity of the reflected light from a normal eye, and the square dots ■ the maximum intensity of the reflected light from the standard white plate. Incidentally, before the correction, the spectral images cannot be obtained with the same light amount and in the same wavelength range. The data obtained with the standard white plate are: a minimum value of 829 and a maximum value of 3532. In spite of the difference, it was confirmed that images were obtained without saturation (leveling off) with the same amount of light. With the normal eye, images of less difference were obtained: a minimum value of 416 and a maximum value of 2217. Incidentally, the above difference in the amount of light lies well within the dynamic range of the CCD camera, which means that photographing with the CCD camera is facilitated and that exposure may be automated.

Figure 10:
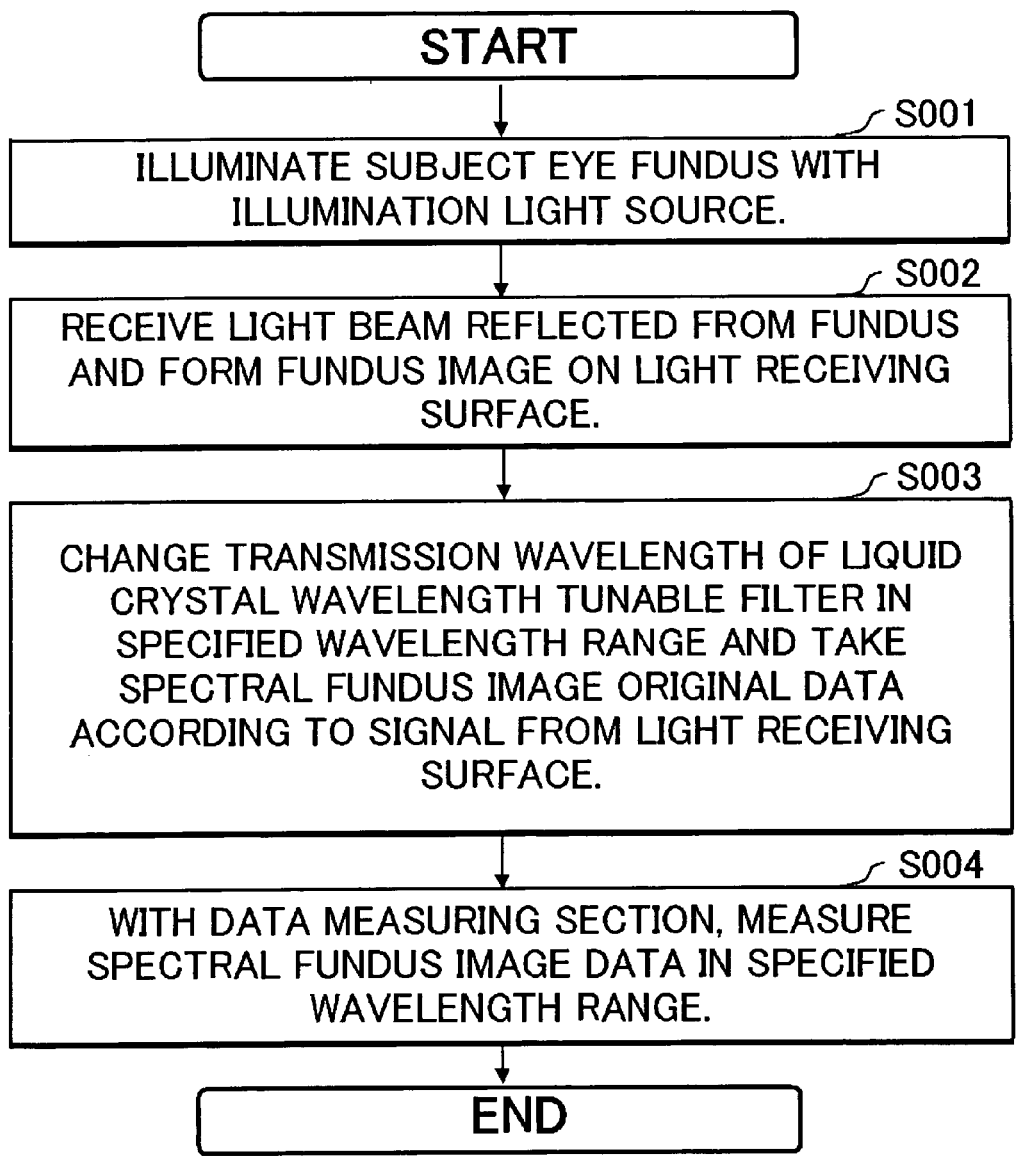
FIG. 10 shows an example flow of a spectral fundus images data measuring method as an embodiment of the invention.

FIG. 10 shows an example flow of the spectral fundus images data measuring method related to the embodiment of the present invention. First, the fundus F of a subject eye E of a human or an animal is illuminated with a light beam from the illumination light source 11 that emits a light beam within a specified wavelength range (step S001). Next, the light receiving surface of the photographing section 4 receives the light beam reflected from the fundus F of the human or animal to form a fundus image (step S002). Next, using the liquid crystal wavelength tunable filter 32 that permits to choose wavelength of the transmitted light beam within a specified wavelength range, the wavelength of the light beam passing through the liquid crystal wavelength tunable filter 32 is changed to obtain spectral fundus images data using the signal from the light receiving surface (step S003). Next, in the data measuring section 7, spectral fundus images data are measured successively in the specified wavelength range (step S004).

Figure 11:
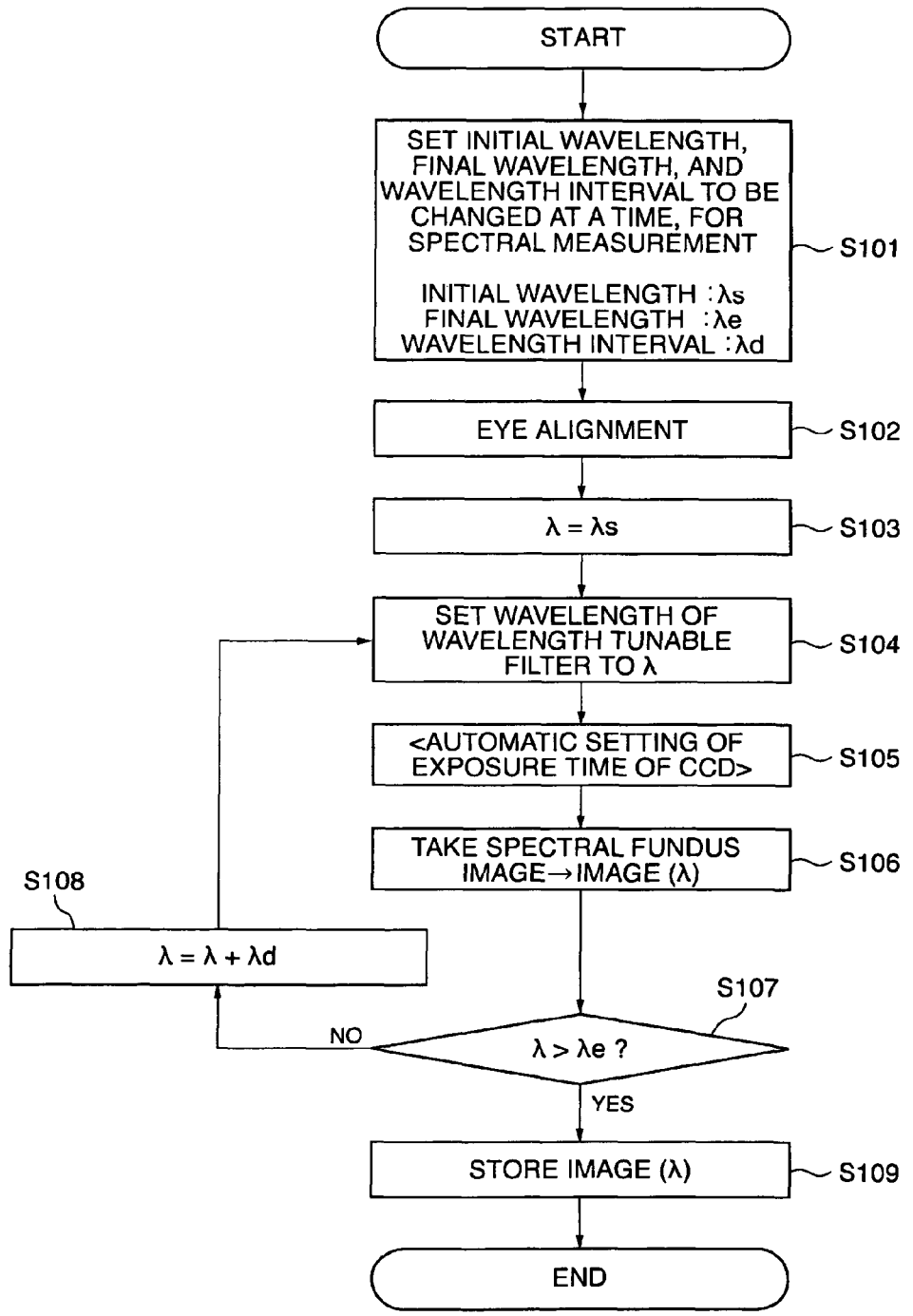
FIG. 11 shows an example flow of taking spectral fundus images.

FIG. 11 shows an example flow of acquiring spectral fundus images. This corresponds to the step S003 of FIG. 10. First, an initial wavelength λs for spectral measurement, a final wavelength λe, and a wavelength interval (amount of change in wavelength) λd to be changed at a time, for spectral measurement are set (step S101). Next, the fundus camera section 2 is aligned with the subject eye E (step S102). Next, the measurement wavelength λ is set to the initial wavelength λs (step S103). The transmission wavelength of the liquid crystal wavelength tunable filter 32 is adjusted to be the measurement wavelength λ (step S104). Exposure time of the CCD camera 34 is automatically set to specified predetermined values for respective measurement wavelengths λ (step S105). Spectral fundus images are taken by automatic exposure for the preset exposure times (step S106). If the measurement wavelength λ is not greater than the final wavelength λe (NO in the step S107), the wavelength interval λd is added to the measurement wavelength λ (step S108) to change the wavelength setting (step S104), and exposure and image-taking are repeated. When the measurement wavelength λ becomes greater than the final wavelength λe (YES in step S107), the obtained fundus images are stored (step S109). This flow of steps for obtaining the spectral fundus images, including the loop steps, may be controlled by a program except for the eye alignment (step S002). The program is stored in the control section 8 so that: the exposure control section 81 controls the exposure of the CCD camera 34, and the wavelength control section 82 controls the wavelength of the liquid crystal wavelength tunable filter 32. The control section 8 also controls the data taking section 71 for data acquisition or the like.

Figure 12:
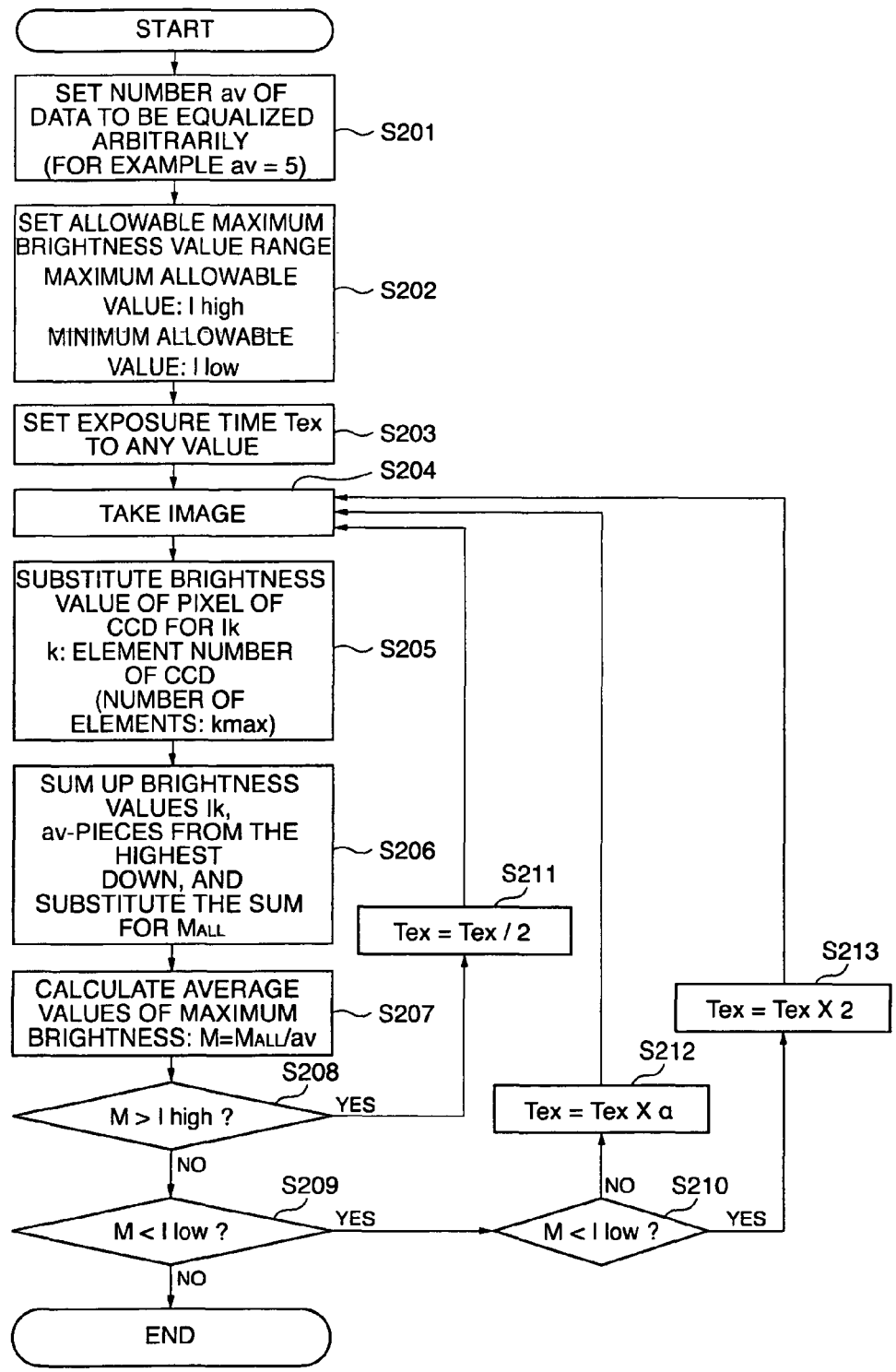
FIG. 12 shows an example flow of setting the exposure time of the CCD camera.

FIG. 12 shows an example flow of setting the exposure time of the CCD camera. This corresponds to the step S105 in FIG. 11. This is to additionally supplement the spectral characteristic flattened by the insertion of the spectral characteristic correcting filter 13 with the exposure time correction of the CCD camera 34. First, a number (av-pieces) of data to be equalized is set arbitrarily (five, for example) (step S201). Allowable maximum brightness value range (maximum allowable value $I_{high}$, minimum allowable value $I_{low}$) is set (step S202). Next, the exposure time $T_{ex}$ is set to an arbitrary value (step S203) to take a spectral fundus image (step S204). For the obtained spectral fundus image, brightness values $I_k$ of respective pixels of the CCD are obtained (CCD element number is assumed to be k, and the number of elements $k_{max}$) (step S205). A preset av-pieces of brightness values $I_k$ are chosen in decreasing order of the value to determine their sum $M_{ALL}$ (step S206) and calculate a maximum brightness mean value $M(=M_{ALL}/av)$ (step S207).

In case the maximum brightness mean value M is greater than the maximum allowable value $I_{high}$ (YES in the step S208), the exposure time is shortened (to ½ in this example) (step 211). In case it is smaller than the minimum allowable value $I_{low}$ (YES in the step S209), the exposure time is increased. In this example, two stages are used. In case it is smaller than a specified value $I_{-low}$ (NO in the step S210), the exposure time is made α-times (for example α=1.2) (step S212). In case it is greater than the specified value $I_{-low}$ (YES in the step S210), the exposure time is made two times (step S213). Then, the process goes back to take images again (step S204). In case the maximum brightness mean value M falls within the preset range (NO in steps S208 and S209), the exposure time is assumed to be appropriate, and the exposure time $T_{ex}$ is set to that value. Thereafter, the set value is used to obtain spectral fundus images (step S204).

As for the newly obtained spectral fundus image, the preset value $T_{ex}$ of exposure time is maintained as long as the maximum brightness mean value M remains within the preset range (NO in the steps S208 and S209), and the preset value is renewed when the mean value falls outside the range. In practice, when taking spectral fundus images, taking them in increasing sequence of wavelength results in slow change in wavelength and less change in spectral fundus images, and less cases occur in which the exposure time is renewed in the above routine. As a result, the process is carried out efficiently to obtain favorable images within a short period of time. Using this flow of CCD camera exposure time setting makes it possible to obtain images of excellent spectral characteristic. In case the spectral characteristic correcting filter 13 is used together, it is also possible to further improve the spectral characteristic. The flow of setting the CCD camera exposure time, including a loop process, may be controlled by a program. The program is stored in the control section 8, so that the exposure control section 81 controls the exposure of the CCD camera 34.

Figure 13:
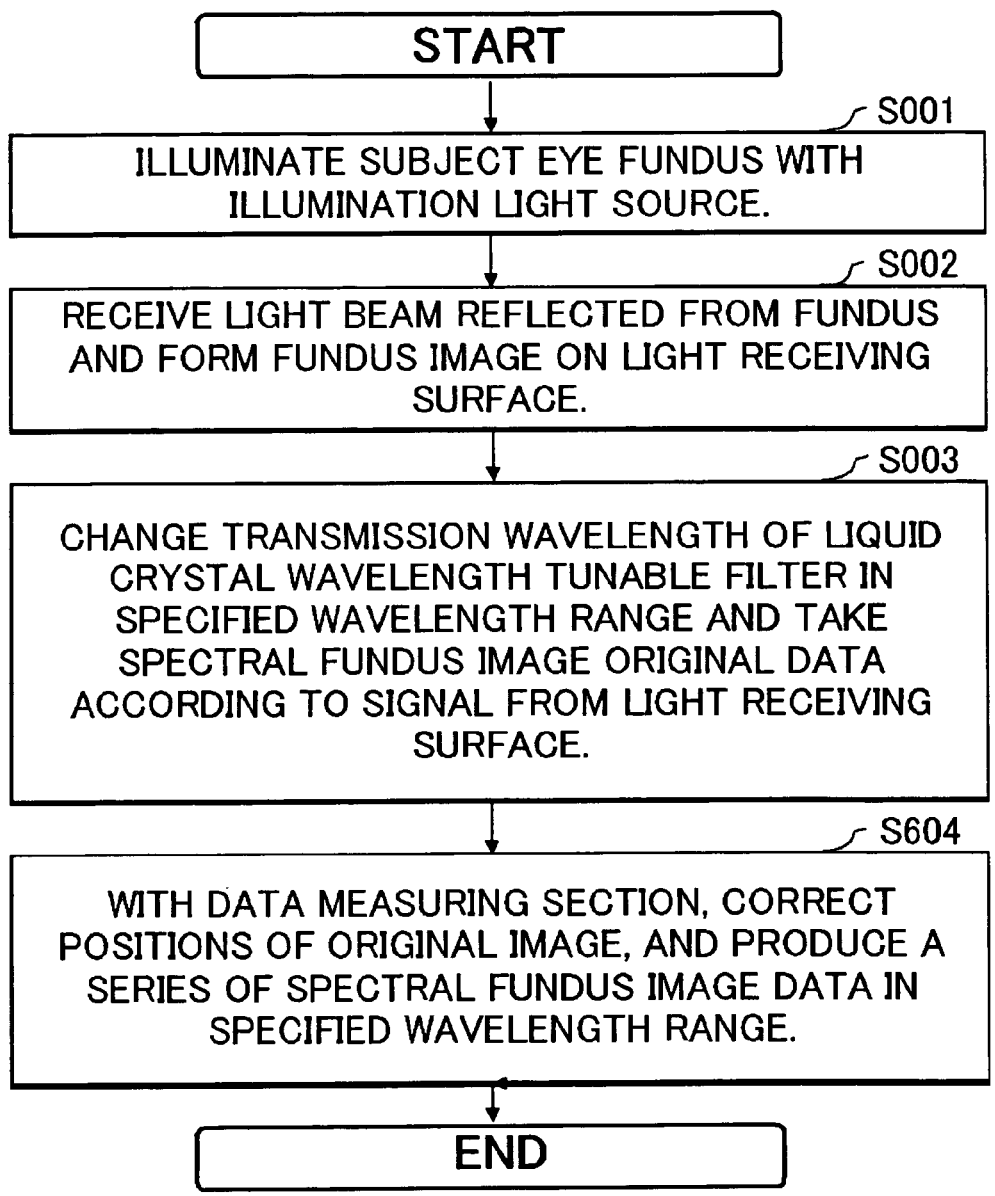
FIG. 13 shows an example flow of the spectral fundus images data measuring method as an embodiment of the invention.

FIG. 13 shows an example flow of the spectral fundus images data measuring method as an embodiment of the invention. First, the fundus F of a subject eye E of a human or an animal is illuminated with a light beam from the illumination light source 11 that emits the light beam within a specified wavelength range (step S001). Next, the light receiving surface of the photographing section 4 receives the light beam reflected from the fundus F of the human or animal to form a fundus image (step S002). Next, using the liquid crystal wavelength tunable filter 32 that permits to choose the wavelength of the transmitted light beam within a specified wavelength range, the wavelength of the light beam passing through the liquid crystal wavelength tunable filter 32 is changed to take spectral fundus images data using the signal from the light receiving surface (step S003). Up to here, the flow is the same as that explained with FIG. 10. Next, in the data measuring section 7, spectral fundus image original data, that are different in wavelength from each other by an amount of change less than a threshold value, are compared with each other to correct positions of the images. This is accumulated in succession to form a series of spectral fundus images data in the specified wavelength range (step S604). Owing to a small amount of change in the wavelength, the difference in light intensity is small between spectral fundus image original data, so that an interrelation can be found easily between two fundus image original data on the same part. This facilitates position correction. Therefore, it is possible to correct positions easily with high accuracy by restricting the amount of change in the wavelength as described above. Applying this method to a number of images successively makes it possible to obtain a series of fundus images data in positional agreement with high accuracy.

Next, spectral fundus images are obtained through the same flow as described with FIG. 11.

The exposure time for the CCD camera is to be set through the same flow as described with FIG. 12.

Figure 14:
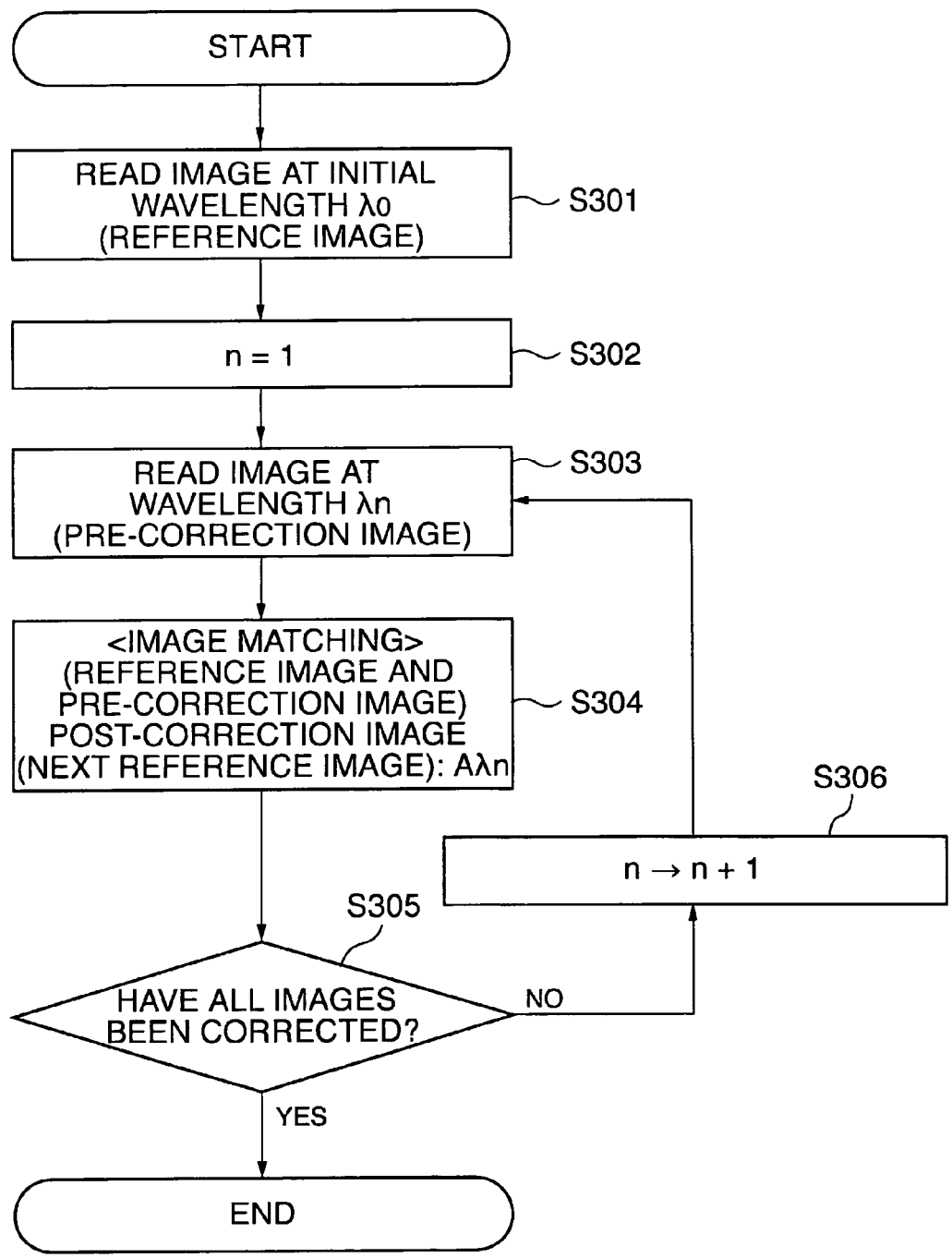
FIG. 14 shows an example flow of matching spectral retinal image positions.

FIG. 14 shows an example flow of matching spectral retinal image positions. This corresponds to the step S604 of FIG. 13. As for taking spectral retinal images, photographing at 10 nm intervals from 510 nm to 720 nm currently takes about 20 seconds under conditions of wavelength tuning time of the liquid crystal wavelength tunable filter 32, the exposure time of the CCD camera 34, etc. During that time, in many cases, undesirable displacements occur in alignment between the subject eye E and the fundus camera 10 and in stationary viewing. As a result, the position of the retinal images taken is displaced, and a position on the retina corresponding to the same coordinates on the light receiving surface of the CCD camera 34 is displaced. Therefore, the position displacement must be corrected before analyzing the oxygen saturation degree. The correction is made by image processing in the data measurement section 7. Besides, the spectral image of the retina changes with the change in the wavelength, and the change in the spectral image is recognizable even at a glance when the wavelength change is large. As a result, images, taken at wavelengths apart from each other, of the same part on the retina, are hard to interrelate. Therefore in this embodiment, alignment is corrected with reduced error as follows: First, position matching is made between two images taken at the shortest and second shortest wavelengths. Next, position matching is made between the images taken at the second shortest and the third shortest wavelengths, like a chain reaction. This image position matching is made in the image correcting section 72 of the data measurement section 7.

First, a fundus image original data is read at an initial (shortest) wavelength $\lambda_0$ to start taking images, and the image read is assumed to be a reference image (step S301). Next, the number (n) of times of image position matching is set to one (step S302). A fundus image original data (next shortest in wavelength to the reference image, called an image at a taking wavelength $\lambda_n$) is read, and the data is assumed to be a pre-correction image (step S303). Then, position matching is done between the reference image and the pre-correction image to correct its position. The pre-correction image with its position corrected is now assumed to be a new reference image (step S304). If any image not corrected remains (NO in the step S305), n is incrementally increased (step S306), a fundus image original data at the next taking wavelength $\lambda_n$ is read (step S303). The image position matching is repeated until the correction is made to all the fundus image original data (YES in the step S305). Incidentally, reading the fundus image original data here may be re-reading the data, already read in the data measurement section 7 from the CCD camera 34 into the data taking section 71, into the image correcting section 72. The flow of spectral retinal image position matching, including the loop process, may be controlled by a program. The program is stored in the data measurement section 7, and the image processing such as the image position matching is carried out in the image correcting section 72.

Figure 15:
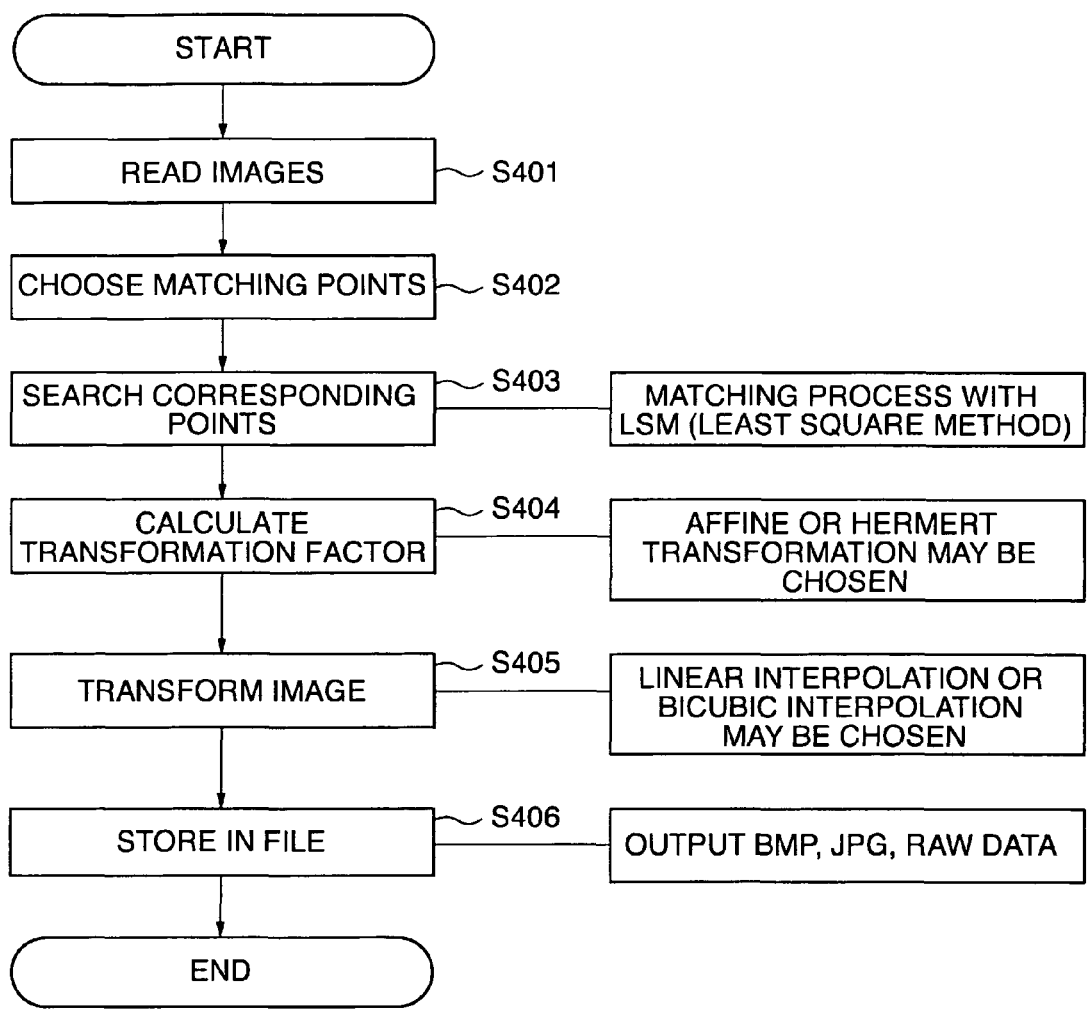
FIG. 15 shows an example flow of image position matching.

FIG. 15 shows an example flow of image position matching. It corresponds mostly to the step S304 of FIG. 14. Two spectral fundus image original data (reference image and pre-correction image) of the illuminated fundus taken at different time points according to signals from the light receiving surface of the photographing section 4 are read (step S401) (This corresponds to the steps S301-S303 of FIG. 14. Steps S402 and after correspond to the step S304 of FIG. 14). Next, a plural number of characteristic points (points that are characteristic and highly conspicuous, may be linear in some cases) are chosen as image matching points from the two images (step S402). Next, positions of corresponding matching points are searched (step S403). For the search, for example the least square method (LSM) is used.

The least square matching is a method in which the position and shape of a template are fixed, and the position and shape of a matching window are changed so that the difference in shade becomes a minimum between the matching window and the template (to establish correlation). For changing the position and shape of the matching window, the affine transformation or Hermert transformation may be chosen. As for these, difference in shade is calculated with varied transformation factors to determine the optimum factor (step S404). Next, transformation of the pre-correction image is carried out using the determined transformation factor (step S405). Here, a linear interpolation method or bicubic interpolation method may be chosen.

The bicubic method is a method for interpolating images and is called cubic interpolation method. As for the scanner in general, many models perform calculation with the primary interpolation method (calculation is made in reference to pixels on a straight line passing two points) or the nearest neighbor method. With the bicubic method, loss of information is the least, and in case of photographic images, the images obtained are smooth and natural. However, it takes much time because of complicated numerical operations. In contrast to the nearest neighbor method in which the value is determined from a single pixel in the neighborhood, the linear interpolation method determines the value from four pixels in the nearest neighborhood, so that interpolation accuracy is high in comparison with the nearest neighbor method.

Next, the image transformed from the pre-correction image is stored in a file (step S406). The stored image is used as a new reference image in the next image matching. The data may be stored for example in BMP format, in JPG format, or may be output as raw data.

Figure 16:
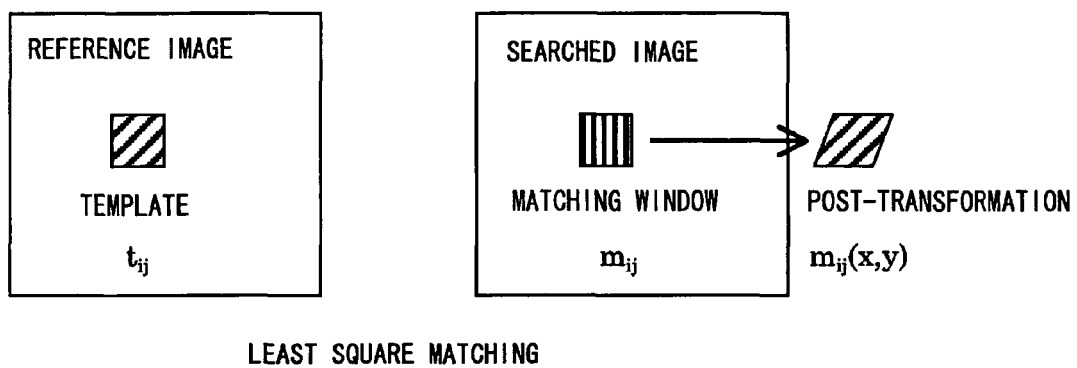
FIG. 16 is a drawing for explaining the least square matching.

FIG. 16 is a drawing for explaining the least square matching. First, a template is made from the reference image, and the initial position of the matching window is determined with a search image. The template of the reference image is assumed to be $t_{ij}$, the matching window of the search image to be $m_{ij}$, and its matching window after transformation to be $m_{ij}(x, y)$.

$$F_{ij}(a1, a2, a3, a4, a5, a6) = m_{ij}(x, y) - t_{ij} \quad \text{Equation(3)}$$

The residual difference $F_{ij}(a1\text{-}a6)$ represents the difference in shade between the template $t_{ij}$ and the matching window $m_{ij}(x, y)$ after geometric 25 transformation. To minimize the residual difference, transformation of the matching window $m_{ij}$ is carried out. While the transformation must be carried out in consideration of the method of projection, here the transformation is carried out using the affine transformation (equation 4) to determine affine coefficients a1-a6 of the matching window:

$$x = a1 + a2 \times i + a3 \times j$$

$$y = a4 + a5 \times i + a6 \times j \quad \text{Equation (4)}$$

First, the equation (3) is made linear.

$$F_{ij}(a1 \sim a6) \doteq F_{ij}(a01 \sim a06) + \frac{F_{ij}(a1 \sim a6)}{\partial a1} \cdot \Delta a1 + \frac{F_{ij}(a1 \sim a6)}{\partial a2} \cdot \Delta a2 + \frac{F_{ij}(a1 \sim a6)}{\partial a3} \cdot \Delta a3 + \frac{F_{ij}(a1 \sim a6)}{\partial a4} \cdot \Delta a4 + \frac{F_{ij}(a1 \sim a6)}{\partial a5} \cdot \Delta a5 + \frac{F_{ij}(a1 \sim a6)}{\partial a6} \cdot \Delta a6 = 0 \quad \text{Equation (5)}$$

Derivatives (partial differential coefficients) for respective variables are as follows:

$$\frac{F_{ij}(a1 \sim a6)}{\partial a1} = gx \cdot i \quad \text{Equation (6)}$$

$$\frac{F_{ij}(a1 \sim a6)}{\partial a2} = gx \cdot j$$

$$\frac{F_{ij}(a1 \sim a6)}{\partial a3} = gx$$

$$\frac{F_{ij}(a1 \sim a6)}{\partial a4} = gy \cdot i$$

$$\frac{F_{ij}(a1 \sim a6)}{\partial a5} = gy \cdot j$$

$$\frac{F_{ij}(a1 \sim a6)}{\partial a6} = gy$$

$$\therefore -F_{ij}(a01 \sim a06) = gxi \cdot \Delta a1 + gxj \cdot \Delta a2 + gx \cdot \Delta a3 + gyi \cdot \Delta a4 + gyj \cdot \Delta a5 + gy \cdot \Delta a6 \quad \text{Equation (7)}$$

With the equation (7) as an observation equation, the matching window is transformed to re-constitute the image. Convergence calculation and image re-constitution are repeated until a convergence reference is reached. In other words, calculation is repeated so that $\Delta a1$-$\Delta a6$ come to minimum values. Here, while the affine coefficients to be actually obtained are a1-a6, obtained coefficients are $\Delta a1$-$\Delta a6$. Therefore, affine coefficients a1-a6 are calculated by adding $\Delta a1$-$\Delta a6$ to the initial values of a1-a6. The position that satisfies the convergence reference is assumed to be the position of the matching window. When the matching window position for the search image is determined, evaluation of corresponding points between images becomes possible.

Next, an example application of the spectral fundus images data measuring method of this embodiment to the spectral retinal image analysis is described. First as a premise, influence of oxygenated hemoglobin and reduced hemoglobin on the spectral fundus images data is described.

Figure 17:
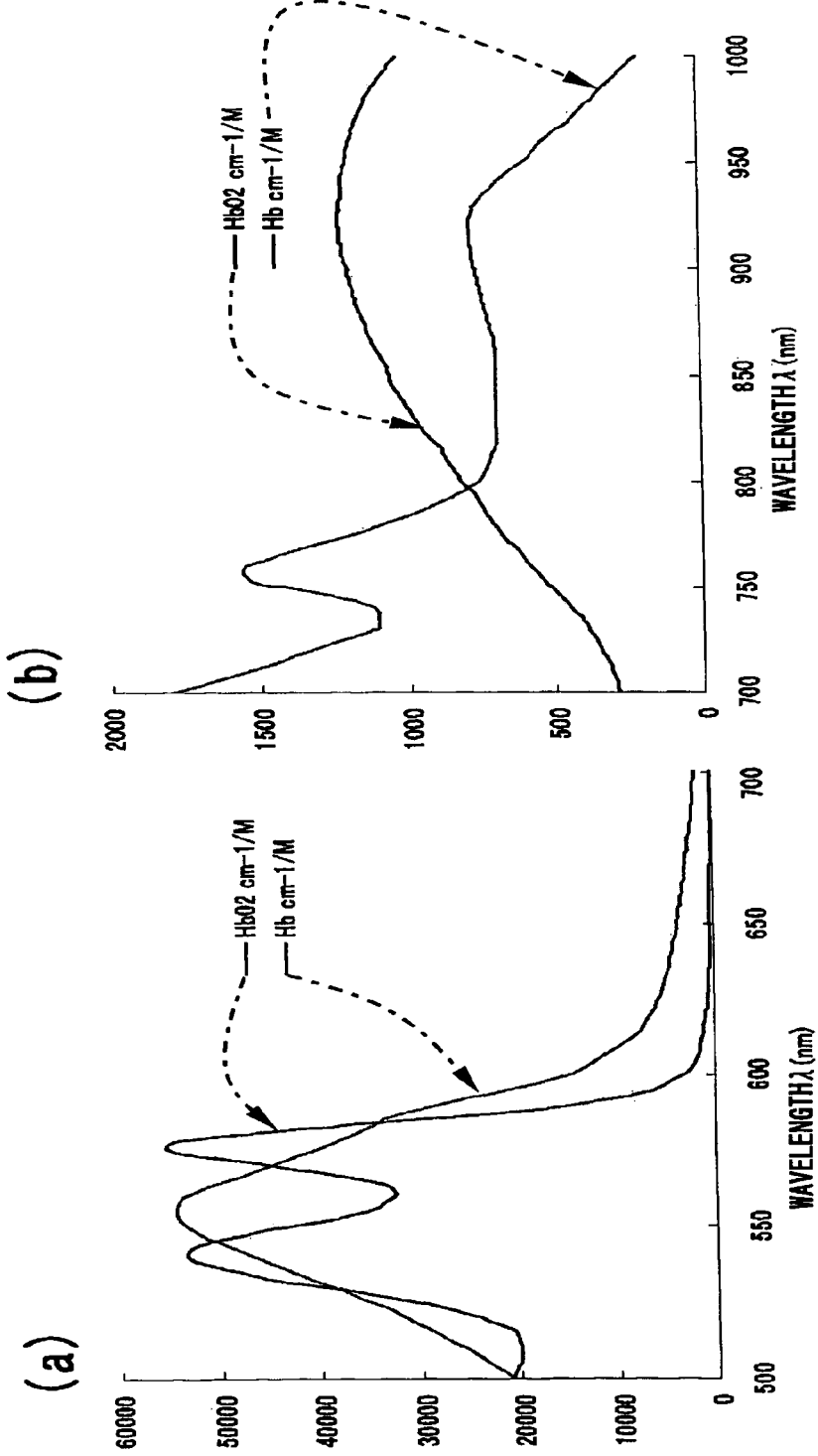
FIG. 17 shows an example of absorbed light amounts of oxygenated hemoglobin and reduced hemoglobin.

FIG. 17 shows an example of absorbed light amounts of oxygenated hemoglobin and reduced hemoglobin (in $cm^{-1}$/moles/liter). FIG. 17(a) shows the absorbed light amount in the visible range and FIG. 17(b) in the near infrared range. Oxygenated hemoglobin is expressed as $HbO_2$ and the reduced hemoglobin as Hb. The oxygen saturation degree analysis for the retina utilizes the presence of wavelength-dependent difference in the amounts of absorbed light with oxygenated hemoglobin and reduced hemoglobin. Analyzing to what extent this spectral characteristic pattern is contained in the spectral characteristic of respective measurement subject parts makes it possible to determine the rates of content of oxygenated hemoglobin and reduced hemoglobin in the measurement subject parts. There is further possibility of finding out the oxygen saturation degree from the rate of oxygenated hemoglobin. This time, a wavelength range of 540 to 610 nm was chosen in which the difference in the amount of light absorption with oxygenated hemoglobin and reduced hemoglobin is large.

The retina contains, in addition to hemoglobin, various other ingredients, having different spectral characteristics respectively. Although they are thought to affect the spectral characteristic, a very simplified algorithm was employed this time to carry out analysis on the assumption of presence of influence of only oxygenated hemoglobin and reduced hemoglobin.

Next, analysis of spectral retinal images is described.

As subject eyes E: (A) a normal eye and (B) an eye affected with branch retinal vein occlusion (BRVO) are chosen for measurement.

Figure 18:
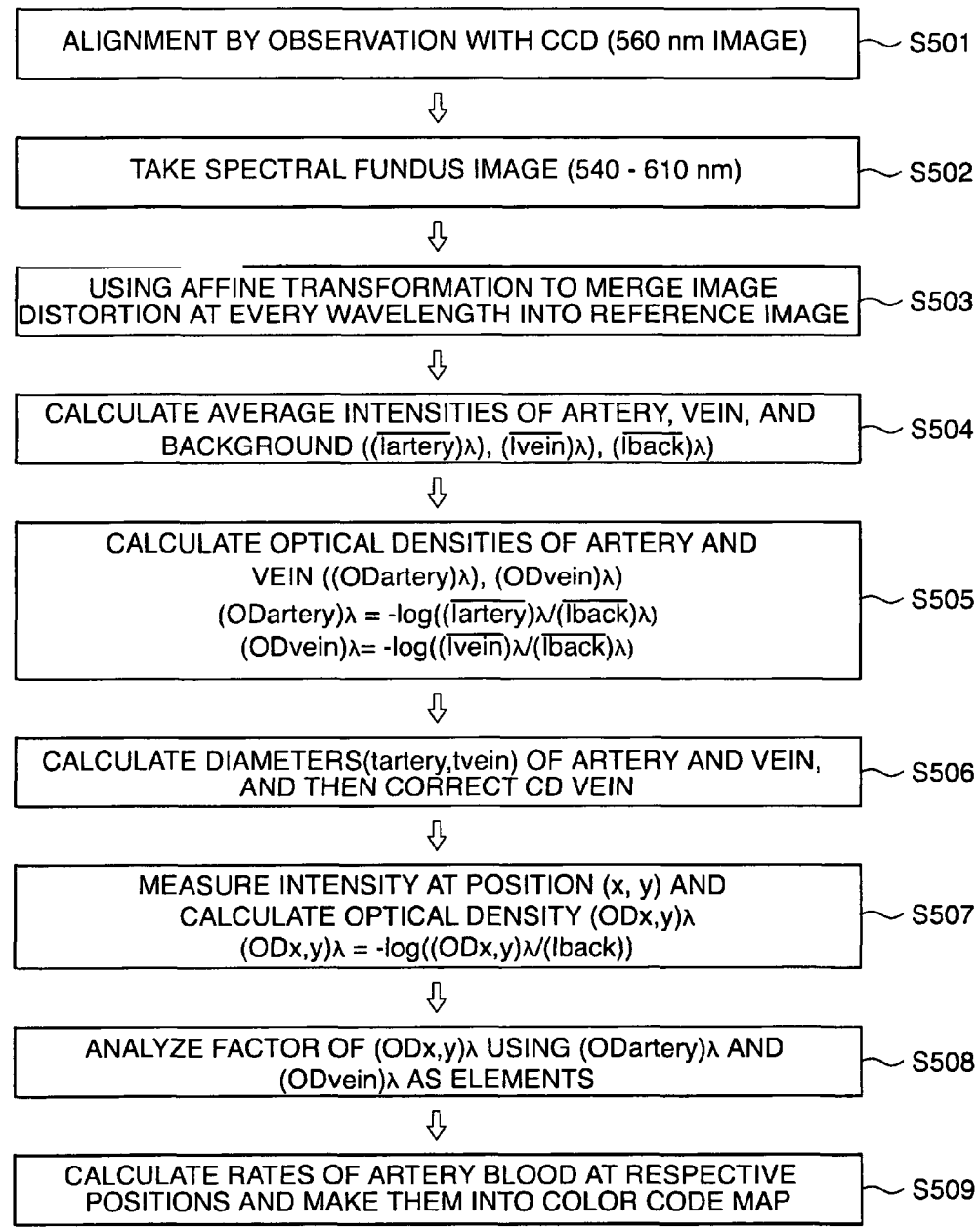
FIG. 18 shows an example flow of spectral retinal image analysis.

FIG. 18 shows an example flow of spectral retinal image analysis. Analysis flow algorithm is as follows:

(a) The subject eye E and the fundus camera section 2 are aligned with each other. The alignment light is lit up to make the alignment (position matching) while watching images taken with the CCD camera 54 (step S501, corresponding to the step S102 of FIG. 11).

(b) Spectral images are taken. While making focus adjustment, spectral fundus images are taken at 10 nm intervals from 540 to 610 nm successively in the order from the short wavelength side (step S502, corresponding to the step S106 of FIG. 11).

(c) Of the images taken, one the shortest in wavelength is assumed to be a reference image. Another the next shortest in wavelength is assumed to be a pre-correction image. Deformation of the pre-correction image is corrected by affine transformation to adapt to the reference image. The transformed image is assumed to be a new reference image, and another image the next shortest in wavelength is assumed to be a new pre-correction image. The correction is carried out successively for images of respective wavelengths (step S503, corresponding to the steps S301 to S306 of FIG. 14).

(d) Average intensities of artery, vein, and background at wavelength $\lambda$ is calculated (step S504):

$$\overline{(I_{artery})_\lambda}, \ \overline{(I_{vein})_\lambda}, \ \overline{(I_{back})_\lambda}$$

(e) Optical densities $((OD_{artery})'_\lambda, (OD_{vein})'_\lambda)$ of artery and vein at wavelength $\lambda$ are calculated (step S505):

$$(OD_{artery})'_\lambda = -\log\left(\frac{\overline{(I_{artery})_\lambda}}{\overline{(I_{back})_\lambda}}\right) \quad \text{Equation (8)}$$

$$(OD_{vein})'_\lambda = -\log\left(\frac{\overline{(I_{vein})_\lambda}}{\overline{(I_{back})_\lambda}}\right)$$

(f) Thicknesses of artery and vein ($t_{artery}$, $t_{vein}$) are measured at the position where the average intensity is measured to correct the optical densities $((OD_{artery})_\lambda, (OD_{vein})_\lambda)$ of artery and vein (step S506):

$$(OD_{artery})_\lambda = \frac{(OD_{artery})'_\lambda}{t_{artery}} \qquad \text{Equation (9)}$$

$$(OD_{vein})_\lambda = -\frac{(OD_{vein})'_\lambda}{t_{vein}}$$

(g) Intensities of local points corresponding to respective coordinate positions (x, y) such as the characteristic points on the retina are measured to calculate the optical densities $((OD_{x,y})_\lambda)$ of artery and vein at respective coordinate positions (x, y) (step S507):

$$(OD_{x,y})_\lambda = -\log\left(\frac{(I_{x,y})_\lambda}{(\overline{I_{back}})_\lambda}\right) \qquad \text{Equation (10)}$$

(h) Using the optical densities of artery and vein $((OD_{artery})_\lambda, (OD_{vein})_\lambda)$ at respective coordinate positions (x, y) at a wavelength λ as elements, factor analysis of the optical density $((OD_{x,y})_\lambda)$ at respective coordinate positions (x, y) on the retina is carried out (step S508).

(i) The rate of arterial blood at respective coordinate positions (x, y) on the retina are calculated to make a color code map of the rate of oxygenated hemoglobin (step S509).

As described above, when the optical density (OD) is calculated, the ratio of the average intensity of artery or vein to the average intensity of background is made, expressed in logarithm, and multiplied by −1, or the ratio of the average intensity of respective positions to the average intensity of background is made, expressed in logarithm, and multiplied by −1. However, the absorption density (AD) may be used instead of the OD, and the value calculated as follows may be used: The average intensity of background is subtracted from the average intensity of artery or vein, which is divided by the average intensity of background; or the average intensity of background is subtracted from the average intensity of respective positions, and the result is divided by the average intensity of background. Here, the absorption density (AD) at any point is expressed with the equation 11:

$$(AD_{x,y})_\lambda = \left(\frac{(I_{x,y})_\lambda - (\overline{I_{back}})_\lambda}{(\overline{I_{back}})_\lambda}\right) \qquad \text{Equation (11)}$$

This spectral retinal image analysis may be controlled with a program. The program is stored in the data measurement section 7. The image analysis is carried out in the image analyzing section 73, and the oxygenated hemoglobin rate, etc. are made into a map in the map forming section 74.

Figure 19:
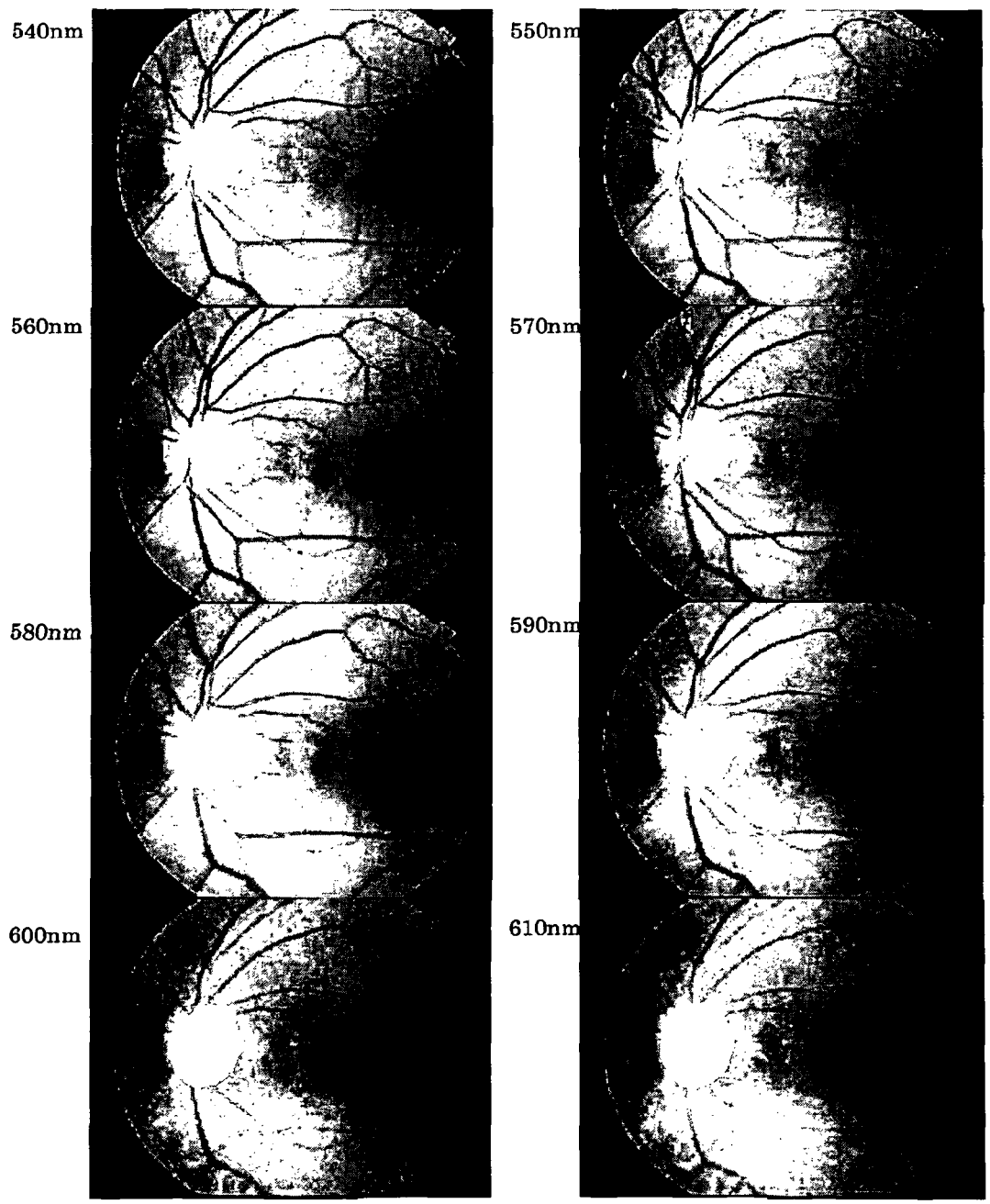
FIG. 19 shows an example of spectral retinal images taken of a normal eye.

FIG. 19 shows an example of spectral retinal images obtained of a normal eye.

Figure 20:
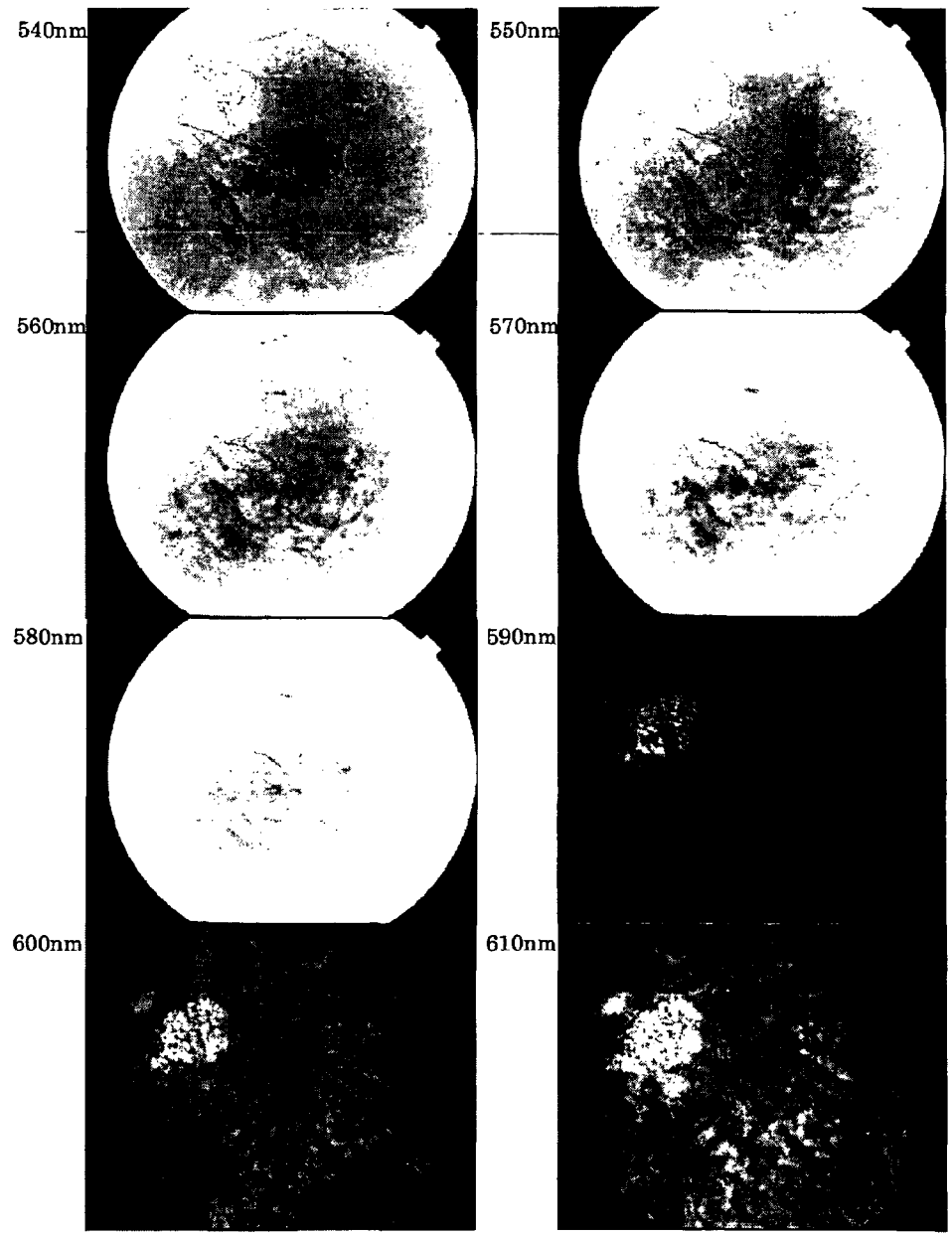
FIG. 20 shows an example of spectral retinal images obtained of an BRVO eye.

FIG. 20 shows an example of spectral retinal images obtained of an BRVO eye.

The images in FIGS. 19 and 20 are those before correction by image matching. The optic disk, blood vessels (arteries and veins), and affected parts are photographed to be discernible. In the Figures, the optic disk is the bright, small circular part; and the blood vessels are dark lines. Because no flash light was used, these images were taken with less amount of light in comparison with ordinary fundus camera. In case measurements are made at wavelength intervals of 10 nm in the wavelength range between 510 to 720 nm, measurement time is about 20 seconds at the longest. However, because a spectral characteristic correcting filter is additionally inserted, the amount of light entering the subject eye is small, so that burden on the subject is not so great. In this way, this embodiment has made it possible to obtain spectral images in a stabilized manner.

Figure 21:
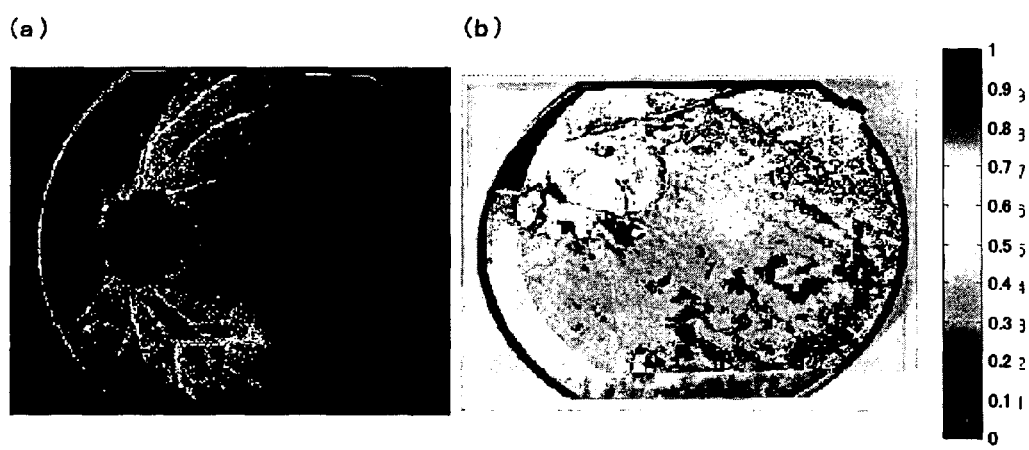
FIG. 21 shows an example of color code map of fundus photographs.

FIG. 21 shows an example of color code map of fundus photographs. FIG. 21(a) is a color code map, showing the results of analysis of the oxygen saturation degree for the normal eye. FIG. 21(b) is a color code map, showing the results of analysis of the oxygen saturation degree for the BRVO eye. The map shows that brighter the color, the more oxygen-saturated. As for the BRVO eye, an area not saturated with oxygen extends in the lower part, which is in agreement with the result of diagnosis. As for the normal eye, an area not saturated with oxygen extends rightward from the fovea, showing that this area is activated.

While an embodiment of the invention is described above, the invention is not limited to the above embodiment; it is apparent that the invention may be embodied in various ways of modification without departing from the gist of the invention.

For example, the constitution of the optical system is not limited to this embodiment. The light source, photographing means, and optical path may be arbitrarily chosen as long as there are provided: an illumination optical system that has an illumination light source emitting a light beam of a specified wavelength range and illuminates the fundus of the subject eye with light beam from the illumination light source, and a light receiving optical system that receives the light beam reflected from the illuminated fundus and forms fundus images on the light receiving surface of the photographing section. Further, the optical system may be provided with a stationary view system for projecting a stationary view target on the fundus. A compensation optical system for compensating aberration of the illumination light may be incorporated. A regulating section for regulating the brightness of the illumination light source may be provided.

Further, the wavelength tunable filter or spectral characteristic correcting filter may be provided in either the illumination optical system or light receiving optical system. While this embodiment is described as an example of using the liquid crystal wavelength tunable filter as a wavelength tunable filter, the wavelength may be changed with a spectral device using a diffraction grating or prism. Further, the spectral characteristic of the spectral characteristic correcting filter varies with the light source, photographing means, and the spectral characteristic of the wavelength tunable filter used, and so is not limited to the blue filter. Further, the light source is not limited to the halogen lamp but any light source capable of emitting a light beam in a specified wavelength range may suffice. The light receiving surface is not limited to the CCD but a CMOS may be used. The spectral measurement wavelength range may be chosen from a range between visible to near infrared ranges. In particular, it is preferable to choose a range in which the spectral distribution characteristic of the light absorption amount of artery or vein varies greatly.

Also in this embodiment, while the order of taking fundus images original data is made successively from shorter wavelength side as an example, the order may be changed.

Figure 22:
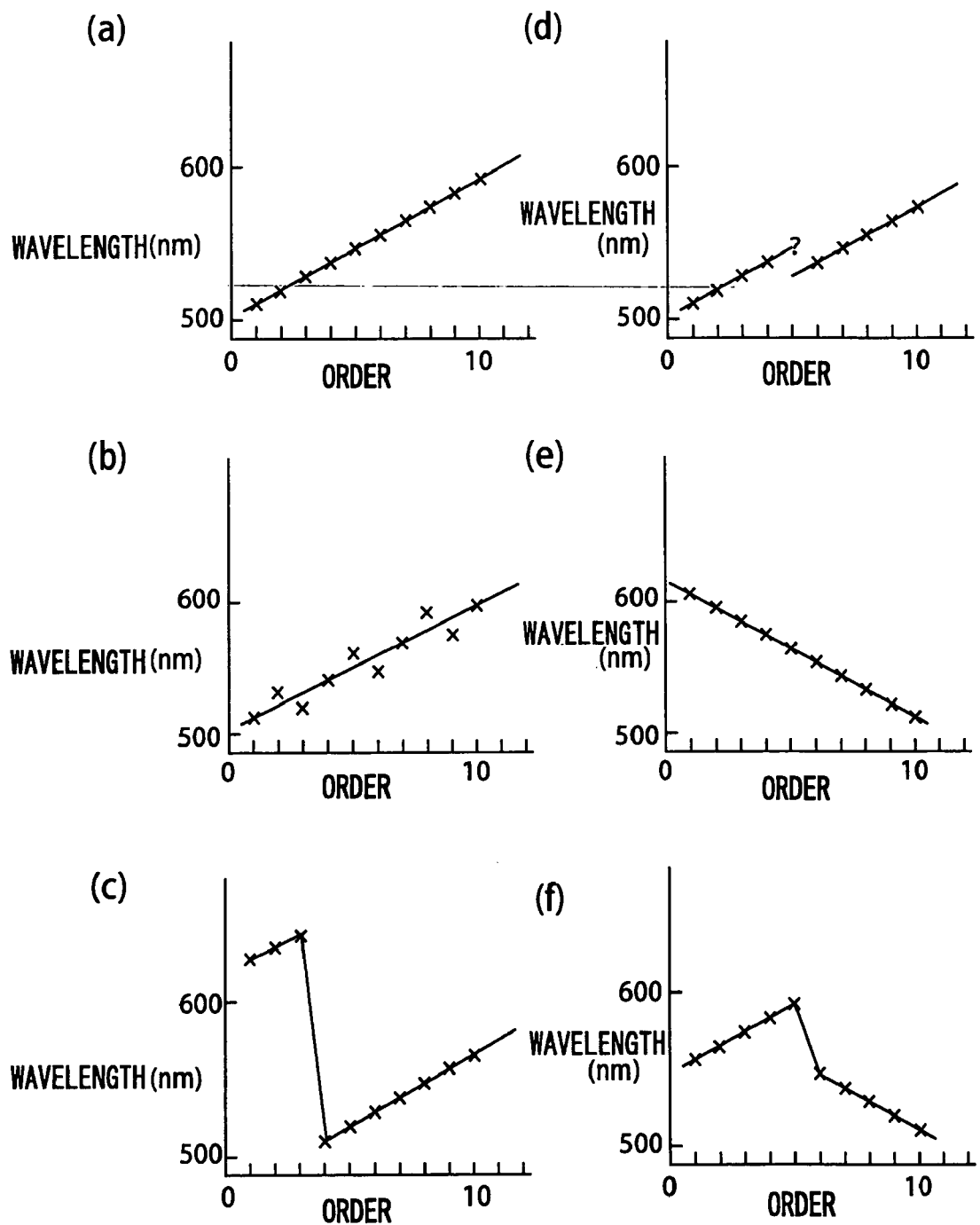
FIG. 22 is a drawing for explaining the order of taking images.

FIG. 22 is a drawing for explaining the order of taking images. FIG. 22(a) shows a case of taking original images in the order from shorter wavelength side. This is an ideal order of taking images. This makes it possible to correct with high accuracy the change in alignment between the eye and apparatus with the lapse of time. In FIG. 22(b) the order does not necessarily depend on whether the wavelength is long or short; in case the wavelength of an adjacent order is close and the amount of change in wavelength does not exceed a threshold value (for example in case the threshold value is 30 nm and the amount of change in wavelength is 10 nm), it is still possible to correct the image position. In FIG. 22(c), the order is discontinued in the middle, and in the discontinued area the image positions are difficult to be corrected. However, the image positions can be corrected in the first group of data and in the second group of data. It can be said also in this case that the image positions are corrected while comparing each other the fundus image original data in a shorter wavelength range as long as the amount of change in wavelength does not exceed a threshold value. FIG. 22(d) shows an example case in which position correction becomes impossible due to some trouble such as the motion of the subject eye in the middle of measurement. In that case, measurement is restarted from the previous wavelength at which an image has already been taken. As a result, two groups, one before the trouble and the other after the trouble, have data at the same wavelength. On the basis of these data, a series of fundus images data, with their positions corrected accurately, can be obtained. FIG. 22(e) shows a case of taking original images in the order from longer wavelength side. This makes it possible, like the case of FIG. 22(a), to correct with high accuracy the change in alignment between the eye and apparatus with the lapse of time.

FIG. 22(f) shows a case in which an image near the median of the measurement wavelength range where relatively stabilized images have been taken is assumed to be a reference image, a next original data of a longer wavelength is assumed to be a pre-correction image, and its position is corrected. The corrected image is assumed to be a new reference image and a next original data of a longer wavelength is assumed to be a pre-correction image, and its position is corrected. In this way, positions are corrected in succession from short to long wavelengths up to the longest wavelength. After that, the image near the median of the measurement wavelength range is assumed again to be the reference image, a next original data of a shorter wavelength is assumed to be a pre-correction image, and its position is corrected. The corrected image is assumed to be a new reference image and a next original data of a shorter wavelength is assumed to be a pre-correction image, and its position is corrected. It is possible, like the case of FIG. 22(a), to correct with high accuracy the change in alignment between the eye and the apparatus with the lapse of time. The same holds true in case the position is corrected first from a wavelength near the median to shorter wavelength and then from the wavelength near the median to longer wavelength.

Further, it is also possible to change the order of steps in this embodiment. For example, while FIG. 11 is described as an example in which the fundus images are stored as a whole after taking spectral fundus images at all the wavelength in the spectral measurement wavelength range, a loop may be employed in which each fundus image is stored immediately after taking the spectral fundus image at each wavelength. Further in FIG. 15, image position matching may be carried out while successively reading fundus images original data (pre-correction images) from the CCD camera, or image position matching may be carried out by reading into the data taking section all the fundus images original data with the data measurement section from the CCD camera while successively re-reading into the image correcting section the fundus image original data (pre-correction images) accumulated in the data taking section.

Further, while an example was described in which the programs for the spectral fundus image taking flow and the CCD camera exposure time setting flow are stored in the control section, and the programs for the spectral retinal image position matching and the spectral retinal image analysis flow are stored in the data measurement section, the control section may hold all of these programs to control the entire spectral fundus images data measurement apparatus including the data measurement section, or the control section may read these programs from an external recording device or CD ROM to control the spectral fundus images data measurement apparatus.

Further, while the influence of ingredients other than hemoglobin was disregarded in the spectral retinal image analysis in this embodiment, an algorithm may be used in which influence of such ingredients are taken into consideration. Further in the image correlation process too, a method may be used that is other than the least square method, simple, and less accurate.

This invention is used in measuring spectral fundus images data.

Here are enumerated reference numerals and symbols of major elements used in the above explanation:
1 spectral fundus images data measuring apparatus
2 fundus camera section
3 top housing section
4 photographing section
5 relay optical system
6 camera relay section
7 data measuring section
8 control section
9 extended section
10 illumination optical system
11 halogen lamp
12 condenser lens
13 spectral characteristic correcting filter
14 diaphragm
15 mirror
16 relay lens
20 light receiving optical system
21 iris diaphragm
22 focusing lens
23 image forming lens
24 mirror
25 switching mirror
31 dichroic mirror
32 liquid crystal wavelength tunable filter
33 image forming lens
34 CCD camera
40 common optical system
41 beam splitter
42 objective lens
50 alignment optical system
51 alignment light source
52 dichroic mirror
53 image forming lens
54 monitoring camera
60 finder optical system
71 data taking section
72 image correcting section
73 image analyzing section
74 map forming section
81 exposure control section
82 wavelength control section
E subject eye
F fundus

What is claimed is:

1. An apparatus for measuring spectral fundus image data, comprising:

an illumination optical system having an illumination light source that emits a light beam in a specified wavelength range, for illuminating a fundus of a subject eye with the light beam from the illumination light source;

a light receiving optical system for receiving the light beam reflected from the illuminated fundus and for forming a fundus image on the light receiving surface of a photographing section;

a wavelength tunable filter disposed in either the illumination optical system or the light receiving optical system and capable of choosing a wavelength of a transmitted light beam in the specified wavelength range;

a spectral characteristic correcting filter disposed in either the illumination optical system or the light receiving optical system and having a wavelength characteristic for correcting the wavelength characteristic of the emitted light intensity of the illumination light source and the transmission wavelength characteristic of the wavelength tunable filter to keep the received light intensity on the light receiving surface within a specified range; and a data measuring section for taking spectral fundus image data based on signals from the light receiving surface when the wavelength of the transmitted light beam of the wavelength tunable filter is changed.

2. The apparatus for measuring spectral fundus image data as recited in claim 1, wherein the wavelength tunable filter is disposed in the light receiving optical system and the spectral characteristic correcting filter is disposed in the illumination optical system.

3. The apparatus for measuring spectral fundus image data as recited in claim 1, wherein the wavelength tunable filter is a liquid crystal wavelength tunable filter and the spectral characteristic correcting filter is constituted that its transmission rate in a specified wavelength range is higher on the shorter wavelength side than on the longer wavelength side.

4. The apparatus for measuring spectral fundus image data as recited in claim 1, wherein the specified wavelength range is 540 to 610 nm.

5. The apparatus for measuring spectral fundus image data as recited in claim 1, wherein the light receiving surface is made of a CCD and the specified range of the received light intensity is within a dynamic range of the CCD.

6. The apparatus for measuring spectral fundus image data as recited in claim 1, further comprising an exposure control section constituted to determine automatically the exposure time according to the received light signal level on the light receiving surface.

7. An apparatus for measuring spectral fundus image data, comprising:

an illumination optical system for illuminating a fundus of a subject eye;

a light receiving optical system for receiving a light beam reflected from the illuminated fundus and for forming a fundus image on a light receiving surface of a photographing section; and a data measuring section for comparing with each other a plurality of spectral fundus image original data taken at different time points based on signals from the light receiving surface to correct positions of the images, and for producing a series of fundus image data with their positions corrected, wherein the correction of positions of the images is performed as position matching between a plurality of the spectral fundus image original data using correlation processing and affine transformation or Hermert transformation while choosing characteristic points.

8. The apparatus for measuring spectral fundus image data as recited in claim 7, wherein the data measuring section chooses, as the characteristic point, a blood vessel part on the shorter wavelength side and the choroid blood vessel part on the longer wavelength side to correct positions of the images.

9. The apparatus for measuring spectral fundus image data as recited in claim 7, wherein the illumination optical system includes an illumination light source that emits a light beam in a specified wavelength range;

further comprising a wavelength tunable filter disposed in either the illumination optical system or the light receiving optical system and capable of choosing a wavelength of a transmitted light beam in the specified wavelength range;

wherein the data measuring section takes a plurality of the fundus image original data by changing a wavelength of the light beam transmitted through the wavelength tunable filter.

10. An apparatus for measuring spectral fundus image data, comprising:

an illumination optical system for illuminating a fundus of a subject eye;

a light receiving optical system for receiving a light beam reflected from the illuminated fundus and for forming a fundus image on a light receiving surface of a photographing section; and a data measuring section for comparing with each other a plurality of spectral fundus image original data taken at different time points based on signals from the light receiving surface to correct positions of the images, and for producing a series of fundus image data with their positions corrected, wherein the illumination optical system includes an illumination light source that emits a light beam in a specified wavelength range;

further comprising a wavelength tunable filter disposed in either the illumination optical system or the light receiving optical system and capable of choosing a wavelength of a transmitted light beam in the specified wavelength range;

wherein the data measuring section takes a plurality of the fundus image original data by changing a wavelength of the light beam transmitted through the wavelength tunable filter.

11. The apparatus for measuring spectral fundus image data as recited in claim 10, further comprising a spectral characteristic correcting filter disposed in either the illumination optical system or the light receiving optical system and having a wavelength characteristic for correcting the wavelength characteristic of emitted light intensity of the illumination light source and the transmission wavelength characteristic of the wavelength tunable filter to keep the received light intensity on the light receiving surface within a specified range.

12. The apparatus for measuring spectral fundus image data as recited in claim 10, wherein the amount of change in the wavelength chosen at the wavelength tunable filter can be set to be equal to or smaller than a threshold value; and the data measuring section corrects the positions of the images while comparing with each other the fundus images original data different in wavelength by the amount of change equal to or smaller than the threshold value.

13. The apparatus for measuring spectral fundus image data as recited in claim 12, wherein the specified wavelength range is 540 to 610 nm, and the amount of change equal to or smaller than the threshold value is 10 nm.

14. The apparatus for measuring spectral fundus image data as recited in claim 10, wherein the wavelength tunable filter is a liquid crystal wavelength tunable filter.

15. The apparatus for measuring spectral fundus image data as recited in claim 10, wherein the data measuring section is capable of calculating the received light intensity and optical density (OD) of artery and vein.

16. The apparatus for measuring spectral fundus image data as recited in claim 15, wherein the data measuring section makes corrections according to a diameter of a blood vessel of a part where intensities at the artery and vein are calculated, calculates ODs in respective positions on the retina, analyzes factors of ODs in respective positions based on spectral distribution of ODs of the artery and vein, calculates rates of oxygenated hemoglobin in respective positions, and makes the oxygenated hemoglobin rates into a map.

17. A method for measuring spectral fundus image data, comprising the steps of:
   illuminating a fundus of a subject eye of an animal with a light beam in a specified wavelength range;
   receiving a reflected light beam from the fundus and forming an animal fundus image;
   changing a wavelength of the light beam in the specified wavelength range to take spectral fundus image data; and
   comparing with each other spectral fundus image original data different in wavelength by an amount of change smaller than a threshold value, and producing a series of spectral fundus image data in the specified wavelength range,
   wherein, when positions of the images are corrected; an original data the second shortest in wavelength with respect to a reference image the shortest in wavelength, out of the spectral fundus image original data, is used as a pre-correction image, the position of which is corrected; next, using the position-corrected pre-correction image as a new reference image, another original data the third shortest in wavelength is used as another pre-correction image, the position of which is corrected; followed by successive correction of positions from a shorter wavelength side to a longer wavelength side,
   wherein, when positions of the images are corrected; an original data the second shortest in wavelength with respect to a reference image the shortest in wavelength, out of the spectral fundus image original data, is used as a pre-correction image, the position of which is corrected; next, using the position-corrected pre-correction image as a new reference image, another original data the third shortest in wavelength is used as another pre-correction image, the position of which is corrected; followed by successive correction of positions from a shorter wavelength side to a longer wavelength side,
   or, an original data the second longest in wavelength with respect to a reference image the longest in wavelength, out of the spectral fundus images original data, is used as a pre-correction image, the position of which is corrected; next, using the position-corrected pre-correction image as a new reference image, another original data the third longest in wavelength is used as another pre-correction image, the position of which is corrected; followed by successive correction of positions from the longer wavelength side to the shorter wavelength side.

18. A method for measuring spectral fundus image data, comprising the steps of:
   illuminating a fundus of a subject eye of an animal with a light beam in a specified wavelength range;
   receiving a reflected light beam from the fundus and forming an animal fundus image;
   changing a wavelength of the light beam in the specified wavelength range to take spectral fundus image data; and
   comparing with each other spectral fundus image original data different in wavelength by an amount of change smaller than a threshold value, and producing a series of spectral fundus image data in the specified wavelength range,
   wherein the spectral fundus image original data images are taken in the specified wavelength range of 540 to 610 nm and with the amount of change in wavelength being set to 10 nm;
   the step of correcting the image positions having the steps of, choosing characteristic points of spectral fundus image original data different in wavelength from each other by an amount corresponding to a change less than a threshold value to match their positions by carrying out correlation processing and affine transformation or Hermert transformation,
   choosing artery and vein as characteristic points to calculate received light intensities and optical densities (ODs) of the artery and vein,
   calculating ODs in respective positions on the retina by corrections according to the blood vessel diameters in parts where the intensities at the artery and vein are calculated,
   calculating the rates of oxygenated hemoglobin in respective positions on the retina by analyzing factors of ODs in respective positions on the retina on the basis of spectral distribution of ODs of the artery and vein, and
   making the rates of oxygenated hemoglobin of the spectral fundus images into a map.

\* \* \* \* \*